(12) United States Patent
Park et al.

(10) Patent No.: US 11,529,317 B2
(45) Date of Patent: Dec. 20, 2022

(54) METHOD OF PREPARING SILICA NANOCAPSULES AND SILICA NANOCAPSULES

(71) Applicant: Agency for Science, Technology and Research, Singapore (SG)

(72) Inventors: Eun Ju Park, Singapore (SG); Alexander M. Van Herk, Singapore (SG); Praveen Thoniyot, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 181 days.

(21) Appl. No.: 16/499,560

(22) PCT Filed: Mar. 28, 2018

(86) PCT No.: PCT/SG2018/050147
§ 371 (c)(1),
(2) Date: Sep. 30, 2019

(87) PCT Pub. No.: WO2018/182518
PCT Pub. Date: Oct. 4, 2018

(65) Prior Publication Data
US 2021/0100753 A1    Apr. 8, 2021

(30) Foreign Application Priority Data
Mar. 30, 2017    (SG) .......................... 10201702634U

(51) Int. Cl.
| *A61K 9/51* | (2006.01) |
| *A61K 8/11* | (2006.01) |
| *A61K 8/25* | (2006.01) |
| *A61Q 19/00* | (2006.01) |

(52) U.S. Cl.
CPC ............ *A61K 9/5192* (2013.01); *A61K 8/11* (2013.01); *A61K 8/25* (2013.01); *A61K 9/5115* (2013.01); *A61Q 19/00* (2013.01); *A61K 2800/413* (2013.01)

(58) Field of Classification Search
CPC .......... A61K 9/5192; A61K 8/11; A61K 8/25; A61K 9/5115; A61K 2800/413; A61K 2800/10; A61K 2800/56; A61K 2800/651; A61Q 19/00; A23P 10/30; B01J 13/14; C01B 33/14
See application file for complete search history.

(56) References Cited

U.S. PATENT DOCUMENTS

2018/0050115 A1*   2/2018  Mou .................... A61K 9/51
2018/0193278 A1*   7/2018  Yu ..................... A61K 9/501

OTHER PUBLICATIONS

Kao et al., Chem. Commun., 2012,48,3454-3456 (Year: 2012).*
Hubert, D. H. W. et al., Vesicle-Directed Growth of Silica. Advanced Materials, Sep. 13, 2000, vol. 12, No. 17, pp. 1286-1290. Abstract Only.
Liu, J. et al., A facile vesicle template route to multi-shelled mesoporous silica hollow nanospheres. Journal of Materials Chemistry, Feb. 17, 2010, vol. 22, No. 11, pp. 4595-4601.
Zhang, L. X. et al., The Effect of Template Phase on the Structures of As-Synthesized Silica Nanoparticles with Fragile Didodecyldimethylammonium Bromide Vesicles as Templates. *Advanced Materials*, Nov. 14, 2007, vol. 19, No. 23, pp. 4279-4283, Abstract Only.
Zhang, Y. et al., "Silica-based nanocapsules: synthesis, structure control and biomedical applications", *Chemical Society Reviews*, Oct. 13, 2014, vol. 44, No. 1, pp. 315-335.
PCT/SG2018/050147 received an International Search Report dated Apr. 10, 2018, 5 pages.
PCT/SG2018/050147 received Written Opinion dated Apr. 10, 2018, 7 pages.
Singapore Application No. SG11201908954Q received a Written Opinion dated Sep. 7, 2020, 7 pages.
Singapore Application No. 11201908954Q received a Second Written Opinion dated Jul. 5, 2021, 6 pages.

* cited by examiner

*Primary Examiner* — Robert S Cabral
(74) *Attorney, Agent, or Firm* — Kilpatrick Townsend & Stockton LLP

(57) ABSTRACT

There is provided a method of preparing silica nanocapsules, the method comprising mixing a surfactant with water at a temperature that is above the gel-to-liquid transition temperature of the surfactant to form a mixture, passing the mixture one or more times through at least one pore to obtain a dispersion of vesicles, and adding a silica precursor to the dispersion of vesicles to form silica nanocapsules. Also provided is a silica nanocapsule formed from a vesicle template, and a method of delivering one or more types of molecules to a subject. In a specific embodiment, hollow silica nanocapsules having substantially lens-shaped are synthesized by employing dimethyldioctadecylammonium bromide (DODAB) or dioctadecyldimethyl ammonium chloride (DODAC) as the vesicle template and tetraethyl orthosilicate (TEOS) as the silica precursor.

10 Claims, 14 Drawing Sheets

METHOD OF PREPARING SILICA NANOCAPSULES AND SILICA NANOCAPSULES

TECHNICAL FIELD

Various embodiments disclosed herein relate broadly to silica nanocapsules, and methods of producing silica nanocapsules.

BACKGROUND

Cargo-carriers have attracted great research interest in the recent years due to their potential use in drug delivery whereby drug molecules are encapsulated within the carrier and delivered to targeted sites of the body. A wide range of natural and synthetic polymers (polymeric carriers, micelles or dendrimers), lipids (liposomes), gold carriers, nanotubes and magnetic carriers have been used as cargo-carriers in drug delivery. However, despite a large number of studies performed on methods to synthesize cargo-carriers, several critical issues remained.

Firstly, there are toxicity concerns regarding cargo-carriers comprising nanoparticles as interactions between nanoparticles and the biological system are believed to potentially cause cytotoxicity. Biocompatibility, biodegradability as well as chemical and physical stability are some of the important considerations when designing methods for synthesizing cargo-carriers that are suitable for use on the human body. However, such properties are not easily achievable.

Next, there is increasing interest in constructing submicron sized hollow particles for use as cargo-carriers but problems such as lack of control over the particle morphology and particle size still present major challenges. Other drawbacks with these conventional methods include formation of unstable colloidal dispersions and low concentrations present in water which result in low solid contents of the products formed.

Currently, methods for synthesizing cargo-carriers may also require chemical treatments with acid/solvents or working with elevated temperatures such as calcination (especially for methods that require the use of polymer/hard templates) in order to prepare hollow particles for cargo loading and delivery. However, the harsh chemical treatment or elevated temperature applied often affect the stability of the shell of the carrier, resulting in particle breakage. These made loading of molecules into the carrier difficult.

Furthermore, scaling up production of cargo-carriers for industrial scale applications using current methods proved challenging due to the costly organic solvents and complex techniques used, which impede the economic production of cargo-carriers for viable industrial uses.

In view of the above, there is thus a need to address or at least ameliorate one of the above problems.

SUMMARY

In one aspect, there is provided a method of preparing silica nanocapsules, the method comprising:
mixing a surfactant with water at a temperature that is above the gel-to-liquid transition temperature of the surfactant to form a mixture;
passing the mixture one or more times through at least one pore to obtain a dispersion of vesicles; and
adding a silica precursor to the dispersion of vesicles to form silica nanocapsules.

In one embodiment, the step of adding a silica precursor to the dispersion of vesicles results in the silica precursor reacting with the vesicles to generate an organic solvent.

In one embodiment, the organic solvent generated from the reaction between the silica precursor and the vesicles causes the shape of the vesicles to change from a substantially spherical shape to a substantially lens shape.

In one embodiment, the surfactant comprises a tetra alkyl ammonium halide.

In one embodiment, the silica precursor comprises a silicon alkoxide.

In one embodiment, the surfactant comprises a tetra alkyl ammonium halide selected from the group consisting of: dimethyldioctadecylammonium bromide (DODAB); dimethyldioctadecylammonium chloride (DODAC); sulfate, phosphate or acetate salt of dimethyldioctadecylammonium (DODAX); dimethyldioctadecenylammonium bromide (DDAB); dimethyldioctadecenylammonium chloride (DDAC); sulfate, phosphate, acetate salt of dimethyldioctadecenylammonium (DDAX); bromide, chloride, sulfate, phosphate or acetate salt of 1,2-dioleoyl-3-trimethylammonium propane (DOTAP); bromide, chloride, sulfate, phosphate or acetate salt of 1,2-dioleoyl-3-dimethylammonium propane (DODAP); bromide, chloride, sulfate, phosphate or acetate salt of N-[1-(2,3-dioleyloxy)propyl]-N,N,N-trimethylammonium (DOTMA), and combinations thereof; and wherein the silica precursor comprises a silicon alkoxide selected from the group consisting of:
tetramethyl orthosilicate (TMOS), tetraethyl orthosilicate (TEOS), tetrapropyl orthosilicate (TPOS), tetrabutyl ortho silicate (TBOS) and combinations thereof.

In one embodiment, the at least one pore has a size of from 100 nm to 1300 nm.

In one embodiment, the step of passing the mixture one or more times through at least one pore comprises passing the mixture one or more times through the at least one pore to reach a dispersion of vesicles having a bluish hue.

In one embodiment, the step of adding a silica precursor to the dispersion of vesicles to form silica nanocapsules is carried out under ambient conditions.

In one embodiment, the step of adding a silica precursor comprises adding the silica precursor to the dispersion of vesicles in an amount such that the surfactant to silica precursor ratio is from 1:5 to 1:40.

In one embodiment, the method further comprises non-thermally drying the silica nanocapsules to obtain a powdered form of silica nanocapsules.

In one embodiment, the method further comprises a step of loading one or more types of cargo molecules into the silica nanocapsules, the step comprising:
subjecting the silica nanocapsules to a solution of the one or more types of cargo molecules; and
coagulating and/or filtrating the silica nanocapsules-containing solution to obtain the loaded silica nanocapsules.

In one embodiment, the method further comprises a step of loading one or more types of cargo molecules into the silica nanocapsules, the step comprising:
mixing the one or more types of cargo molecules with the silica nanocapsules in the presence of a first organic solvent and a second organic solvent to obtain the loaded silica nanocapsules,
wherein the one or more types of cargo molecules is miscible with the first organic solvent, wherein the one or more types of cargo molecules is not miscible with the second organic solvent and wherein the first and second organic solvents are miscible with each other.

In one embodiment, the step of mixing comprises mixing the one or more types of cargo molecules with the nanocapsules in the presence of a first organic solvent prior to adding the second organic solvent.

In one embodiment, the one or more types of cargo molecules comprises a hydrophilic active molecule.

In one embodiment, the method is substantially devoid of the addition of an organic solvent, the addition of a strong acid, the use of etching and the use of calcination, for the removal of a template used to form the silica nanocapsules.

In one embodiment, the silica nanocapsules are substantially lens-shaped.

In one aspect, there is provided a silica nanocapsule formed from a vesicle template, the silica nanocapsule comprising:

a porous silica shell; and a substantially hollow core that is capable of carrying one or more types of cargo molecules in an amount that is at least 20% by weight of the silica nanocapsule.

In one embodiment, the silica nanocapsule is substantially lens-shaped.

In one embodiment, the silica nanocapsule further comprises one or more types of cargo molecules disposed in the substantially hollow core.

In one embodiment, the one or more types of cargo molecules comprises a hydrophilic active molecule.

In one embodiment, the one or more types of cargo molecules are selected from the group consisting of therapeutic agents, diagnostic agents, pharmaceutical agents, cosmetic agents, cosmeceutical agents, nutraceutical agents and combinations thereof.

In one embodiment, the silica nanocapsule has a silky feel to skin.

In one embodiment, the silica nanocapsule comprises one or more of the following properties: biodegradable, biocompatible, non-toxic, hypoallergenic, non-immunogenic and more stable than a spherical microcapsule.

In one aspect, there is provided a method of delivering one or more types of molecules to a subject, the method comprising:

administering to the subject the silica nanocapsule as disclosed herein, the silica nanocapsule comprising the one or more types of molecules disposed within its substantially hollow core.

Definitions

The term "nanocapsule" as used herein broadly refers to a particle having dimensions in the nanoscale and which contains a substantially hollow compartment that is capable of being loaded with a cargo.

The term "surfactant" as used herein broadly refers to a substance or compound that lowers the surface tension when dissolved in water or water solutions, or that reduces interfacial tension between two liquids, or between a liquid and a solid. A "surfactant" may include a compound or substance containing both hydrophilic and hydrophobic groups and is capable of forming vesicles when dissolved in water or water solutions. The term "surfactant" thus includes anionic, cationic, nonionic, zwitterionic and/or amphoteric substance or compound. The term encompasses but is not limited to quaternary ammonium compounds. Examples of such compounds are dimethyldioctadecylammonium bromide (DODAB); dimethyldioctadecylammonium chloride (DODAC); sulfate, phosphate or acetate salt of dimethyldioctadecylammonium (DODAX); dimethyldioctadecenylammonium bromide (DDAB); dimethyldioctadecenylammonium chloride (DDAC); sulfate, phosphate, acetate salt of dimethyldioctadecenylammonium (DDAX); bromide, chloride, sulfate, phosphate or acetate salt of 1,2-dioleoyl-3-trimethylammonium propane (DOTAP); bromide, chloride, sulfate, phosphate or acetate salt of 1,2-dioleoyl-3-dimethylammonium propane (DODAP); bromide, chloride, sulfate, phosphate or acetate salt of N-[1-(2,3-dioleyloxy)propyl]-N,N,N-trimethylammonium (DOTMA) and the like.

The term "gel-to-liquid transition temperature (Tm)" as used herein broadly refers to a temperature that is sufficient to induce a phase change from gel state to liquid state.

The term "porous" as used herein broadly refers a material with a plurality of pores (holes or openings). A "porous" material may be nanoporous, microporous, mesoporous or macroporous.

The term "nano" as used herein is to be interpreted broadly to include dimensions in a nanoscale, i.e., the range of between about 1 nm and about 1000 nm.

Accordingly, the term "nanocapsule", "nanoparticle", "nano lens", "nanocarrier", "nano powder" and the like as used herein may include structures that have at least one dimension in the range of no more than said range. The term "nanocapsule", "nanoparticle", "nano lens", "nanocarrier", "nano powder" and the like as used herein may include structures that have at least one dimension that is no more than about 1000 nm, no more than about 900 nm, no more than about 800 nm, no more than about 700 nm, no more than about 600 nm, no more than about 500 nm, no more than about 400 nm, no more than about 300 nm, no more than about 200 nm, no more than about 100 nm, or no more than about 50 nm. For example, a nanocapsule may have one dimension in the nanoscale, such as the diameter of the capsule, which may be between about 1 nm and about 1000 nm, and the thickness of the capsule may be greater than this range.

The term "particle" as used herein broadly refers to a discrete entity or a discrete body. The particle described herein can include an organic, an inorganic or a biological particle. The particle used described herein may also be a macro-particle that is formed by an aggregate of a plurality of sub-particles or a fragment of a small object. The particle of the present disclosure may be spherical, substantially spherical, or non-spherical, such as lens-shaped, substantially lens-shaped, irregularly shaped particles or ellipsoidally shaped particles. The term "size" when used to refer to the particle broadly refers to the largest dimension of the particle. For example, when the particle is substantially spherical, the term "size" can refer to the diameter of the particle; or when the particle is substantially non-spherical, the term "size" can refer to the largest dimension of the particle.

The term "and/or", e.g., "X and/or Y" is understood to mean either "X and Y" or "X or Y" and should be taken to provide explicit support for both meanings or for either meaning.

The terms "coupled" or "connected" when used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

DESCRIPTION OF EMBODIMENTS

Exemplary, non-limiting embodiments of a method of preparing silica nanocapsules, related silica nanocapsule(s) and method of delivering one or more types of molecules to a subject are disclosed hereinafter.

In various embodiments, there is provided a method of preparing silica nanocapsules, the method comprising: mixing a surfactant with water at a temperature that is above the gel-to-liquid transition temperature of the surfactant to form a mixture; passing the mixture one or more times through at least one pore to obtain a dispersion of vesicles; and adding a silica precursor to the dispersion of vesicles to form silica nanocapsules.

In various embodiments, the dispersion of vesicles serves as soft templates for the subsequent formation of nanocapsules. As compared with methods that involve forming a silica shell around a hard template e.g. a polymer template and subsequently removing the core template through harsh treatment such as using an organic solvent or a strong acid, etching or calcination to leave behind the hollow silica particle product, embodiments of the method disclosed herein provide a simpler method of preparing a hollow silica particle or a silica nanocapsule directly from a soft vesicle template without the need for a subsequent harsh etching and/or calcination step which not only does not remove the template completely in some instances, but also compromises the integrity of the hollow silica particle product in some instances. Embodiments of the method disclosed herein may also be easily scaled up without requiring any specialized external energy input to provide a high temperature.

In various embodiments therefore, the steps of the method are substantially devoid of the addition of an organic solvent, the addition of a strong acid, the addition of any harsh chemical reagents, or the use of a high temperature for the purposes of dissolution/removal of a template. In various embodiments, the method is also substantially devoid of a calcination step and/or an etching step. In various embodiments, the method is substantially devoid of step that is carried out at more than about 70° C., more than about 80° C., more than about 90° C., more than about 100° C., more than about 110° C., more than about 120° C. or more than about 130° C. In various embodiments therefore, the method is substantially devoid of the addition of an organic solvent, the addition of a strong acid, the use of etching and the use of calcination for the removal of a template such as the vesicle or the surfactant used to form the silica nanocapsules, from the silica nanocapsules.

In one embodiment, the method comprises a step of removing the template by washing. The washing may be performed with a liquid medium, for e.g. water or an organic solvent such as an alcohol or combinations thereof. The template may be removed by washing with a mixture of water and ethanol. In other embodiments, the method does not include a step of removing the template. It may be appreciated that in some embodiments, removal of template may not be necessary as the template is substantially hollow and does not impede subsequent processing steps such as loading of cargo.

In various embodiments, the surfactant comprises an amphiphilic molecule. In some embodiments, the surfactant comprises an amphiphilic quaternary ammonium compound.

In various embodiments, the surfactant comprises a quaternary ammonium compound represented by the following formula:

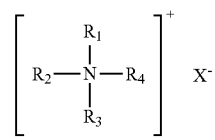

wherein $R_1$, $R_2$, $R_3$ and $R_4$ are independently linear, branched, saturated or unsaturated hydrocarbon groups optionally substituted with a heteroatom such as O, S and P atoms; and wherein $X^-$ is a halide, sulfate, phosphate or acetate.

One or more $R_1$, $R_2$, $R_3$ and $R_4$ may be short chain alkyl groups, with the number of carbon atoms being at least 1, at least 2, at least 3, at least 4, at least 5 or at least 6. One or more of $R_1$, $R_2$, $R_3$ and $R_4$ may be long chain alkyl groups, with the number of carbon atoms being not less than 6, not less than 7, not less than 8, not less than 9, not less than 10, not less than 11, not less than 12, not less than 13, not less than 14, not less than 15, not less than 16, not less than 17, not less than 18, not less than 19, not less than 20, not less than 21 or not less than 22. In some embodiments, $R_1$, $R_2$, $R_3$ and $R_4$ are independently linear, branched, saturated or unsaturated $C_1$-$C_{22}$ hydrocarbon groups optionally substituted with O atom. Accordingly, one or more of $R_1$, $R_2$, $R_3$ and $R_4$ may be the hydrophobic tail(s) of the surfactant that provides the capability of the surfactant to self-assemble into a vesicle type configuration when placed in an aqueous solution.

In some embodiments, $R_1$, $R_2$ and $R_3$ are short chain $C_1$-$C_5$ alkyl groups, and $R_4$ is a long chain $C_6$-$C_{22}$ alkyl group optionally substituted with a heteroatom. In some embodiments, both $R_1$ and $R_2$ are short chain $C_1$-$C_5$ alkyl groups, and both $R_3$ and $R_4$ are long chain $C_6$-$C_{22}$ alkyl groups optionally substituted with a heteroatom. In some embodiments, $R_1$ is a short chain $C_1$-$C_5$ alkyl group, and $R_3$, $R_2$ and $R_4$ are long chain $C_6$-$C_{22}$ alkyl groups optionally substituted with a heteroatom.

In some embodiments, $R_1$ and $R_2$ are short chain $C_1$-$C_5$ alkyl groups, $R_3$ and $R_4$ are long chain $C_6$-$C_{22}$ alkyl groups, and $X^-$ is a halide selected from the group consisting of $F^-$, $Cl^-$, $Br^-$ and $I^-$.

In some embodiments, $R_1$ is the same as $R_2$. In some embodiments, $R_3$ is the same as $R_4$.

In one embodiment, $R_1$ and $R_2$ are both methyl, $R_3$ and $R_4$ are both $C_{18}$ straight chain alkyl groups, and $X^-$ is $Cl^-$ or $Br^-$. For example, the surfactant may be dimethyldioctadecylammonium bromide (DODA-B) or dimethyldioctadecylammonium chloride (DODA-C).

In one embodiment, the surfactant has a or resembles a chemical formula shown as follows:

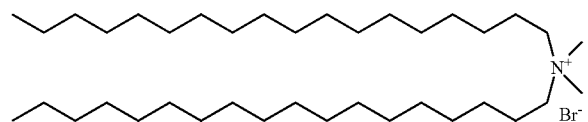 [SMILES: CCCCCCCCCCCCCCCCCC[N+](C)(C)CCCCCCCCCCCCCCCCCC ; [Br-]]

In various embodiments, the amphiphilic quaternary ammonium compound is selected from the group consisting of dimethyldioctadecylammonium bromide (DODAB); dimethyldioctadecylammonium chloride (DODAC); sulfate, phosphate or acetate salt of dimethyldioctadecylammonium (DODAX); dimethyldioctadecenylammonium bromide (DDAB); dimethyldioctadecenylammonium chloride (DDAC); sulfate, phosphate, acetate compound of dimethyldioctadecenylammonium (DDAX); bromide, chloride, sulfate, phosphate or acetate salt of 1,2-dioleoyl-3-trimethylammonium propane (DOTAP); bromide, chloride, sulfate, phosphate or acetate salt of 1,2-dioleoyl-3-dimethylammonium propane (DODAP); bromide, chloride, sulfate, phosphate or acetate salt of N-[1-(2,3-dioleyloxy)propyl]-N,N,N-trimethylammonium (DOTMA); and the like and combinations thereof. In various embodiments, the surfactant comprises a tetra alkyl ammonium halide. In various embodiments, the tetra alkyl ammonium halide comprises two short chain alkyl groups having up to about 5 carbons, two long chain alkyl groups having about 6 to about 22 carbons, and a halide group selected from the group consisting of fluorine, chlorine, bromine and iodine. In one embodiment, the surfactant comprises DODAB. As may be appreciated, the surfactants disclosed herein above may form unilamellar vesicles in water. As may be further appreciated, DODAB is less toxic than an ether type surfactant. In various embodiments therefore, the surfactant selected for the method is one that is substantially non-toxic to the human or animal body. In various embodiments, the surfactant selected for the method is one where its toxicity does not change regardless of or is independent of its form (e.g. present as liquid crystals or gels).

In one embodiment, the vesicles are unilamellar vesicles. In various embodiments, the membrane of unilamellar vesicles comprises the surfactant. In various embodiments, the membrane of unilamellar vesicles comprises a bilayer of amphipilic molecules.

In various embodiments, the mixing step is carried out at a temperature that is from about 45° C. to about 100° C., from about 50° C. to about 100° C., from about 55° C. to about 100° C., from about 60° C. to about 100° C., from about 60° C. to about 90° C., from about 60° C. to about 80° C., from about 60° C. to about 70° C. or from about 60° C. to about 65° C. In some embodiments, the temperature is more than about 44° C. In one embodiment, the temperature is about 60° C. As may be appreciated, in various embodiments, the temperature should be above the gel-to-liquid transition temperature or melting temperature of the surfactant, under which the surfactants may be poorly or substantially not soluble in water.

In some embodiments, the method further comprises a step of agitating the mixture during or after the mixing step. In various embodiments, the step of agitating the mixture comprises stirring the mixture. In various embodiments, stirring the mixture comprises stirring the mixture at a constant stirring speed of about 200 revolutions per minute (rpm), about 250 rpm, about 300 rpm, about 350 rpm or about 400 rpm. In various embodiments, stirring the mixture comprises stirring the mixture for a time period of at least about 15 hours, about 16 hours, about 17 hours, about 18 hours, about 19 hours or about 20 hours. Other manners of agitating the mixture may also be employed. For example, methods of bubbling, shaking, spinning, vortexing or the like may also be used.

In various embodiments, the at least one pore has a size such that, when the mixture of surfactant and water is passed through the pore, a dispersion of vesicles in the nano size range may be obtained. In various embodiments, the at least one pore has a size of no more than about 2000 nm, no more than about 1900 nm, no more than about 1800 nm, no more than about 1700 nm, no more than about 1600 nm, no more than about 1500 nm, no more than about 1400 nm or no more than about 1300 nm. In various embodiments, the at least one pore has a size of from about 100 nm to about 1300 nm, from about 100 nm to about 1200 nm, from about 100 nm to about 1100 nm, from about 100 nm to about 1000 nm, from about 100 nm to about 900 nm, from about 100 nm to about 800 nm, from about 150 nm to about 700 nm, from about 200 nm to about 600 nm, from about 250 nm to about 550 nm, from about 300 nm to about 500 nm, or from about 200 nm to about 400 nm. In one embodiment, the at least one pore has a size of from about 100 nm to about 1300 nm.

In various embodiments, the at least one pore is provided in the form of a membrane. In some embodiments, the membrane comprises a porous membrane or a filter membrane. In various embodiments, the membrane has average pore sizes of no more than about 2000 nm, no more than about 1900 nm, no more than about 1800 nm, no more than about 1700 nm, no more than about 1600 nm, no more than about 1500 nm, no more than about 1400 nm or no more than about 1300 nm. In various embodiments, the membrane has average pore sizes in the range of from about 100 nm to about 1300 nm, from about 100 nm to about 1200 nm, from about 100 nm to about 1100 nm, from about 100 nm to about 1000 nm, from about 100 nm to about 900 nm, from about 100 nm to about 800 nm, from about 150 nm to about 700 nm, from about 200 nm to about 600 nm, from about 250 nm to about 550 nm, from about 300 nm to about 500 nm, from about 350 nm to about 450 nm or from about 200 nm to about 400 nm. In various embodiments, the membrane comprises a polymer optionally selected from the group consisting of polyvinylidene fluoride, polytetrafluoroethylene, polyethylene, polycarbonate, polypropylene, polyamide, polysulfone and the like and combinations thereof. Other materials that are sufficiently resilient to withstand the pressure of filtering or passing the mixture across the membrane may also be used to make the membrane. Accordingly, in various embodiments, the method comprises the use of a membrane extrusion technique. Advantageously, such techniques are capable of controlling the size of the vesicles in a simple, effective and reproducible manner.

The at least one pore may also be provided in a form other than a membrane. For example, the pore may be part of a channel that allows passage of the mixture therethrough and upon extrusion from said channel, a dispersion of vesicles in the nano size range may be obtained. Accordingly, the pore may be part of a micro/nano fluidic device or the like.

In various embodiments, the step of passing the mixture through the at least one pore to obtain the dispersion of vesicles comprises applying a pressure differential across opposite sides of the pore, for example across opposite sides of the membrane containing the pore. In some embodiments, the step of applying a pressure differential across the pore comprises applying a gas or a vacuum to create the pressure differential. Accordingly, the pressure may be applied as a positive (expulsion) or negative pressure (suction). In some embodiments, the gas is applied at a pressure that is more than atmospheric pressure such as for example, in the range of from more than about 1 bar to about 10 bars, from about 2 bars to about 9 bars, from about 3 bars to about 8 bars, or from about 4 bars to about 7 bars. In one embodiment, the gas is applied at a pressure of about 7 bars. In various embodiments, the gas comprises air, nitrogen and/or argon. In one embodiment, the step of passing the mixture through the at least one pore is carried out in a pressurized vessel.

In various embodiments, the passing step is carried out at a temperature that is above the gel-to-liquid transition temperature of the surfactant, optionally at a temperature that is from about 45° C. to about 100° C., from about 50° C. to about 100° C., from about 55° C. to about 100° C., from about 60° C. to about 100° C., from about 60° C. to about 90° C., from about 60° C. to about 80° C. or from about 60° C. to about 70° C. In one embodiment, the temperature is from about 60° C. to about 65° C.

In various embodiments, the step of passing the mixture one or more times through at least one pore is repeated until desirable vesicles are obtained. For example, the step may be repeated until a substantially homogenous dispersion of vesicles is obtained, until the vesicles obtain a substantially uniform size distribution and/or until the vesicles are reduced to certain size range in the nano range. In various embodiments, the step of passing the mixture one or more times through at least one pore is repeated to obtain a substantially monodispersity of the vesicles prior to the step of adding a silica precursor to the dispersion of vesicles. The polydispersity index (PDI) of the dispersion of the vesicles obtained after the passing step may be no more than about 0.5, no more than about 0.4, no more than about 0.3, no more than about 0.20, no more than about 0.19, no more than about 0.18, no more than about 0.17, no more than about 0.16, no more than about 0.155, no more than about 0.14, no more than about 0.13, or no more than about 0.125. In various embodiments, the PDI of the mixture prior to the step of passing the mixture one or more times through at least one pore is more than the PDI after the passing step. For example, the PDI of the mixture prior to the step of passing the mixture one or more times through at least one pore is more than about 0.5. The Z-average size of the dispersion of the vesicles obtained after the passing step may be no more than about 1000 nm, no more than about 900 nm, no more than about 800 nm, no more than about 700 nm, no more than about 600 nm, no more than about 500 nm, no more than about 400 nm, no more than about 300 nm, no more than about 200 nm, no more than about 180 nm, no more than about 150 nm, no more than about 130 nm or no more than about 100 nm. In various embodiments, the Z-average size of the mixture prior to the step of passing the mixture one or more times through at least one pore is more than the Z-average size after the passing step. For example, the Z-average size of the mixture prior to the step of passing the mixture one or more times through at least one pore is more than about 1000 nm.

In various embodiments, the step of passing the mixture one or more times through at least one pore comprises the steps of: (i) passing the mixture through at least one pore to obtain a first pore filtrate; (ii) collecting the first pore filtrate; (iii) passing the first pore filtrate through the at least one pore to obtain a second pore filtrate, and optionally repeating steps (ii) and (iii) one or more times to obtain a third pore filtrate or a further pore filtrate, wherein the final pore filtrate is dispersion of vesicles to which the silica precursor is added to. Optionally, in various embodiments, a step of determining the size of the vesicles, for example, by dynamic light scattering (DLS) may be carried out after each passing step. In various embodiments, the step of passing the mixture one or more times through at least one pore is carried out at least two times, at least three times, at least four times, at least five times, at least six times, at least seven times or at least eight times. In various embodiments, the step of passing the mixture one or more times through at least one pore comprises passing the mixture through the at least one pore one or more times to reach a dispersion of vesicles having a bluish hue/colour. In various embodiments, the bluish hue/colour may be observed by an unaided/naked human eyes under normal (white) lighting conditions. Advantageously, the bluish shine of the dispersion may be used as a rough measure of attainment of a monomodal distribution in a desired size range e.g. size range of about 200 nm before a further characterization of the size and size distribution of the vesicular particles in the dispersion using dynamic light scattering may optionally be carried out. In various embodiments, the step of passing the mixture one or more times through at least one pore comprises passing the mixture through the at least one pore one or more times until a dispersion of vesicles having a distribution in the size range of about 100 nm to about 300 nm is obtained. In various embodiments, the step of passing the mixture through at least one pore comprises an extrusion process. Advantageously, embodiments of the method allow for the tuning of the particle sizes of the vesicles and therefore the tuning of the particle sizes of the resulting silica nanocapsules.

In various embodiments, the method comprises a step of lowering the temperature of the dispersion of vesicles e.g. cooling the dispersion of vesicles to room temperature prior to the step of adding a silica precursor. In various embodiments therefore, the step of adding a silica precursor to the dispersion of vesicles to form silica nanocapsules is carried out under ambient conditions such as ambient/room temperature and pressure.

In various embodiments, the step of adding a silica precursor to the dispersion of vesicles results in the silica precursor reacting with the vesicles to generate an organic solvent. In various embodiments, the organic solvent generated from the reaction between the silica precursor and the vesicles causes the shape of the vesicles to change from a substantially spherical shape to a substantially lens shape. As may be appreciated, in various embodiments, the vesicles formed from mixing the surfactant with water and before the addition of a silica precursor are substantially spherical in shape. Without being bound by theory, it is believed that, in various embodiments, when the silica precursor is added to the dispersion of vesicles to form silica nanocapsules, the silica precursor hydrolyses and condenses to form a silica ($SiO_2$) layer around the vesicles, and during this hydrolysis and condensation reaction, an organic solvent, e.g. ethanol, is produced leading to shape change of the vesicles from a substantially spherical shape to a substantially lens shape.

In some embodiments, the step of adding a silica precursor to the dispersion of vesicles comprises a step of agitating the mixture of silica precursor and vesicles, for example, by vigorous stirring. Optionally, the step of adding a silica precursor may comprise a step of adding an acid or a base as a pH adjuster to control the growth of the silica layer. Without being bound by theory, it is believed that pH influences the sol-gel chemistry of silica growth. In one embodiment, the step of adding a silica precursor may comprise a step of adding ammonia as a pH adjuster.

In various embodiments, the silica precursor comprises a silicon alkoxide. In various embodiments, the silicon alkoxide is selected from the group consisting of tetramethyl orthosilicate (TMOS), tetraethyl orthosilicate (TEOS), tetrapropyl orthosilicate (TPOS), tetrabutyl orthosilicate (TBOS) and the like and combinations thereof. In some embodiments therefore, the surfactant comprises a tetra alkyl ammonium halide selected from the group consisting of: dimethyldioctadecylammonium bromide (DODAB); dimethyldioctadecylammonium chloride (DODAC); sulfate, phosphate or acetate salt of dimethyldioctadecylammonium (DODAX); dimethyldioctadecenylammonium bromide (DDAB); dimethyldioctadecenylammonium chloride (DDAC); sulfate, phosphate, acetate salt of dimethyldioctadecenylammonium (DDAX); bromide, chloride, sulfate, phosphate or acetate salt of 1,2-dioleoyl-3-trimethylammonium propane (DOTAP); bromide, chloride, sulfate, phosphate or acetate salt of 1,2-dioleoyl-3-dimethylammonium propane (DODAP); bromide, chloride, sulfate, phosphate or acetate salt of N-[1-(2,3-dioleyloxy)propyl]-N,N,N-trimethylammonium (DOTMA), and combinations thereof; and the silica precursor comprises a silicon alkoxide selected from the group consisting of: tetramethyl orthosilicate (TMOS), tetraethyl orthosilicate (TEOS), tetrapropyl orthosilicate (TPOS), tetrabutyl ortho silicate (TBOS) and combinations thereof. In various embodiments, the step of adding a silica precursor comprises adding the silica precursor to the dispersion of vesicles in an amount such that the surfactant to silica precursor ratio is from about 1:5 to about 1:40 or at a ratio of about 1:10, or at a ratio of about 1:20, at a ratio of about 1:30.

In various embodiments, the method further comprises drying the silica nanocapsules to obtain a powdered form of silica nanocapsules. In various embodiments, the step of drying the silica nanocapsules does not require the application of heat or thermal energy. Accordingly, in various embodiments, the method further comprises non-thermally drying the silica nanocapsules to obtain a powdered form of silica nanocapsules. In some embodiments, the step of non-thermally drying the silica nanocapsules comprises freeze drying the silica nanocapsules and/or air drying the silica nanocapsules and/or drying the silica nanocapsules with a rotary evaporator and/or spray drying the silica nanocapsules.

In various embodiments, the method further comprises a step of loading one or more types of molecules, for example one or more types of cargo molecules, into the silica nanocapsules to obtain loaded silica nanocapsules. In some embodiments, the step of loading one or more types of molecules into the silica nanocapsules comprises loading the one or more types of molecules through the pore of a porous silica wall of the silica nanocapsules.

In some embodiments, the step of loading one or more types of molecules into the silica nanocapsules comprises subjecting the silica nanocapsules to a solution of the one or more types of molecules, and coagulating and/or filtrating the silica nanocapsules-containing solution to obtain the loaded silica nanocapsules.

In some embodiments, the step of loading one or more types of molecules into the silica nanocapsules comprises: mixing a first organic solvent, a second organic solvent, the nanocapsules, and the one or more types of molecules together, wherein the one or more types of molecules is miscible with/soluble in the first organic solvent, the one or more types of molecules is not miscible with/soluble in the second organic solvent and the first and second organic solvents are miscible with each other. In some embodiments, the step of mixing a first organic solvent, a second organic solvent, the nanocapsules, and the one or more types of molecules together comprises providing the one or more types of molecules and the nanocapsules in first organic solvent prior to mixing with the second organic solvent. In some embodiments, the step of mixing a first organic solvent, a second organic solvent, the nanocapsules, and the one or more types of molecules together is carried out under ambient conditions.

In some embodiments, the step of loading one or more types of molecules, for example one or more types of cargo molecules, into the silica nanocapsules comprises: mixing the one or more types of molecules with the silica nanocapsules in the presence of a first organic solvent and a second organic solvent to obtain the loaded silica nanocapsules, wherein the one or more types of cargo molecules is miscible with the first organic solvent, wherein the one or more types of cargo molecules is not miscible with the second organic solvent and wherein the first and second organic solvents are miscible with each other. In some embodiments, the step of mixing comprises mixing the one or more types of molecules with the nanocapsules in the presence of a first organic solvent prior to adding the second organic solvent.

As may be appreciated, because the first organic solvent is miscible with second organic solvent but the cargo molecule is not miscible with the second organic solvent, the addition of the second organic solvent may dissolve the first organic solvent to leave behind the insoluble cargo molecule in the silica nanocapsules. In some embodiments, the step of adding the second organic solvent comprises a step of agitating, for example by stirring, the mixture of the first organic solvent, the second organic solvent, the one or more types of cargo molecules and the silica nanocapsules for a time period of, for example, for at least about 10 minutes, at least about 20 minutes, at least about 30 minutes, at least about 40 minutes, at least about 50 minutes or at least about 60 minutes.

In some embodiments, the first organic solvent comprises an alcohol. In one embodiment, the alcohol comprises ethanol. In some embodiments, the second organic solvent comprises an ester. In one embodiment, the ester comprises ethyl acetate (EA).

In various embodiments, the one or more types of cargo molecules comprises a hydrophilic/hydrophilic active molecule. Advantageously, embodiments of the methods of preparing silica nanocapsules enable easy and efficient loading of hydrophilic actives which is difficult to achieve in conventional preparation.

In various embodiments, the method further comprises washing the loaded silica nanocapsules. In some embodiments, washing the loaded silica nanocapsules comprises rinsing the loaded silica nanocapsules at least about one time, at least about two times, at least about three times, at least about four times or at least about five times in the second organic solvent.

In various embodiments, the method further comprises drying the loaded silica nanocapsules. In some embodiments, drying the loaded silica nanocapsules comprises drying the loaded silica nanocapsules at room temperature.

In various embodiments, the silica nanocapsules are loaded with the one or more types of cargo molecules at a loading capacity of at least about 20%, at least about 30%, at least about 40%, at least about 50%, at least about 60% or at least about 65%.

Advantageously, embodiments of the method are capable of synthesizing silica nanocapsules with a high loading capacity.

In various embodiments, the steps prior to the step of loading one or more types of cargo molecules into the silica nanocapsules are substantially devoid of the addition of an organic solvent.

In various embodiments, the method is capable of synthesizing silica nanocapsules with a high reproducibility as compared to conventional methods of synthesizing silica spherical microcapsules.

In one embodiment, the method comprises an industrial method. In one embodiment, the method is a scalable method.

In various embodiments, there is provided a silica nanocapsule formed from a vesicle template. In various embodiments, the vesicle template comprises a unilamellar vesicle. In various embodiments, the vesicle template is substantially spherical in shape. In various embodiments, the vesicle template is substantially spherical in shape in solution form when viewed with a conventional transmission electron microscopy (TEM) and/or cryogenic transmission electron microscopy (Cryo-TEM).

In various embodiments, the silica nanocapsule comprises a porous silica shell; and a substantially hollow core configured to contain one or more types of molecules.

In various embodiments, the silica nanocapsules have a configuration in which an outer shell encapsulates a substantially hollow interior/core. In various embodiments, the substantially hollow interior is configured to allow loading of one or more types of molecules.

In some embodiments therefore, there is provided a silica nanocapsule formed from a vesicle template, the silica nanocapsule comprising: a porous silica shell; and a substantially hollow core that is capable of carrying one or more types of cargo molecules in an amount that is at least about 20%, at least about 30%, at least about 40%, at least about 50%, at least about 60% or at least about 65% by weight of the silica nanocapsule. Advantageously, embodiments of the silica nanocapsule have a high loading capacity.

In various embodiments, the silica nanocapsule further comprises one or more types of cargo molecules disposed in the substantially hollow core. In various embodiments, the one or more types of cargo molecules comprises a hydrophilic/hydrophilic active molecule.

In various embodiments, the one or more types of cargo molecules are actives capable of providing a therapeutic effect, a cosmetic effect, a salubrious or health promoting/maintaining effect, a prophylactic effect or combinations thereof. In some embodiments, the one or more types of cargo molecules are selected from the group consisting of therapeutic agents, diagnostic agents, pharmaceutical agents, cosmetic agents, cosmeceutical agents, nutraceutical agents and combinations thereof. In some embodiments, the one or more types of cargo molecules are selected from the group consisting of therapeutics, moisturizers, anti-agers, additives, surfactants, dyes, water soluble dyes, essential oils, vitamins, water soluble vitamins (e.g. vitamin B, vitamin B6, vitamin C, riboflavin), a natural material and combinations thereof. In one embodiment, the one or more types of cargo molecules comprises glycerol.

In some embodiments thereof, the silica nanocapsule is a dermal carrier and/or a drug carrier.

In various embodiments, the silica nanocapsule comprises a dried silica nanocapsule. In various embodiments, the silica nanocapsule comprises a non-thermally dried nanocapsule, a freeze dried silica nanocapsule, an air-dried silica nanocapsule, a rotary evaporator dried silica nanocapsule, a spray-dried silica nanocapsule or combinations thereof.

As may be appreciated, dried silica nanocapsules in powder form may not be compatible by inhalation. In various embodiments therefore, the silica nanocapsule is configured to prevent or minimize its inhalation. In various embodiments, the silica nanocapsule has a density sufficient to prevent or minimize its dispersion in air. In various embodiments, the silica nanocapsule comprising one or more types of cargo molecules has a density sufficient to prevent or minimize its dispersion in air.

In various embodiments, the silica nanocapsules are aspherical-shaped or substantially lens-shaped or ellipsoidal-shaped nanocapsules. In various embodiments, the aspherical-shaped or substantially lens-shaped or ellipsoidal-shaped nanocapsules have a shape resembling a convex set bounded by two circular arcs joined to each other at their endpoints. In various embodiments, the silica nanocapsules are substantially lens-shaped. In various embodiments, the silica nanocapsules are substantially lens-shaped when viewed with a cryogenic transmission electron microscopy (Cryo-TEM) or scanning electron microscope (SEM) or both. In some embodiments, the silica nanocapsules may be observed as substantially lens-shaped in at least one viewing orientation.

In various embodiments, an average of a longest dimension of the silica nanocapsule is in the range of from about 1 nm to about 900 nm, from about 50 nm to about 800 nm, from about 100 nm to about 800 nm, from about 100 nm to about 700 nm, from about 150 nm to about 600 nm, from about 200 nm to about 400 nm, from about 200 nm to about 300 nm or from about 190 nm to 250 nm. In various embodiments, the capsular thickness of the silica nanocapsule is in the range of from about 1 nm to about 500 nm, from about 3 nm to about 300 nm, from about 3 nm to about 200 nm, from about 3 nm to about 100 nm, from about 3 nm to about 50 nm, from about 5 nm to about 300 nm, from about 5 nm to about 200 nm, from about 5 nm to about 100 nm, or from about 5 nm to about 50 nm. As may be appreciated, the small size of the silica nanocapsule endows unique properties to the nanocapsule as compared to its larger counterpart. For example, as compared to its larger counterpart, the silica nanocapsule is less susceptible to breakage, provides better ease in hydrophilic active loading and gives a smoother, more flawless look and a more pleasant feel when applied to the skin.

In various embodiments therefore, the silica nanocapsule(s) has a silky feel to skin. In various embodiments, the silica nanocapsule(s) has a talc-like feel to skin or a feel to the skin that is similar to talcum.

In various embodiments, the silica nanocapsule comprises one or more of the following properties: biodegradable, biocompatible, non-toxic, hypoallergenic, non-immunogenic and more stable than a spherical microcapsule. In various embodiments, the silica nanocapsule is more stable than a spherical microcapsule at a given condition. In various embodiments, the silica nanocapsule is more thermodynamically stable than a spherical microcapsule. In various embodiments, the silica nanocapsule is thermally stable. The silica nanocapsule may be capable of withstanding decomposition and may remain stable to a temperature of at least about 100° C., of at least about 110° C., of at least about 120° C., of at least about 130° C., of at least about 140° C., of at least about 150° C., of at least about 160° C., of at least about 170° C., of at least about 180° C., of at least about 190° C., or of at least about 200° C. In various embodiments, the silica nanocapsule is more chemically and/or physically stable than a spherical microcapsule for example when subject to the same environmental conditions. The silica nanocapsules may be dried for long term storage and subsequently suspended in solution to obtain a stable colloidal formulation. The drying of silica nanocapsules for long term storage may be performed using freeze drying. In some embodiments, the dried silica nanocapsules are taken out from storage and re-suspended in liquid media. The liquid media may be water, an organic solvent such as an alcohol or any other suitable liquid medium. In some embodiments, the dried silica nanocapsules are loaded with glycerol and subsequently re-suspended by emulsifying techniques. In various embodiments, the silica nanocapsule is chemically inert, biologically inert, mesoporous and/or oil absorbent. Advantageously, these properties make embodiments of the silica nanocapsule appealing as therapeutic, cosmetic or personal care products.

In various embodiments therefore, there is provided a therapeutic, cosmetic or personal care product comprising the silica nanocapsule. In various embodiments, the therapeutic, cosmetic or personal care product comprising the silica nanocapsule may prevent or alleviate skin dryness, cracking, itching, scaling, peeling, wrinkling, inflammation, oiliness, loose oil control and the like which may be caused by genetic factors, hormonal changes (e.g. due to ageing), weather, working environment etc. In various embodiments, the cosmetic or personal care product comprises a skin brightening product or a skin hydration product.

Accordingly, in various embodiments, there is provided a therapeutic or cosmetic method comprising administering the silica nanocapsule to a subject, optionally wherein the subject is a mammal, further optionally wherein the mammal is a human. In various embodiments, the method is also non-therapeutic. In various embodiments, the method is also non-diagnostic.

In various embodiments, there is also provided a method of delivering one or more types of molecules to a subject, the method comprising: administering to the subject the silica nanocapsule, the silica nanocapsule comprising the one or more types of molecules disposed within its substantially hollow core. The silica nanocapsule may release all of or at least a portion of the one or more types of molecules disposed within its substantially hollow core at a predetermined time, interval and/or environment. The release may be one of an immediate release, delayed release, controlled release, sustained release, extended release, targeted release or induced release. Therefore, in various embodiments, the silica nanocapsule loaded with cargo is capable of releasing its cargo in a sustained manner or otherwise, over a period of at least about 10 minutes, at least about 20 minutes, at least about 30 minutes, at least about 40 minutes, at least about 50 minutes, at least about 60 minutes, at least about 70 minutes, at least about 80 minutes, at least about 90 minutes, at least about 100 minutes, at least about 110 minutes, or at least about 120 minutes. The step of administering the silica nanocapsule to the subject may comprise administering the silica nanocapsule to the skin, epidermis and/or dermal layer of the subject.

In various embodiments, there is provided a method or a silica nanoparticle as described herein.

BRIEF DESCRIPTION OF FIGURES

FIGS. 5,6 and 7 are microscopic images of the synthesized silica nanocapsules in accordance with various embodiments disclosed herein.

FIG. 5 shows a conventional transmission electron microscopy (TEM) image of the hollow silica lens structure in solutions in accordance with various embodiments disclosed herein.

DETAILED DESCRIPTION OF FIGURES

Example embodiments of the disclosure will be better understood and readily apparent to one of ordinary skill in the art from the following discussions and if applicable, in conjunction with the figures. It should be appreciated that other modifications related to structural and chemical changes may be made without deviating from the scope of the disclosure. Exemplary embodiments are not necessarily mutually exclusive as some may be combined with one or more embodiments to form new exemplary embodiments.

Figure 1:
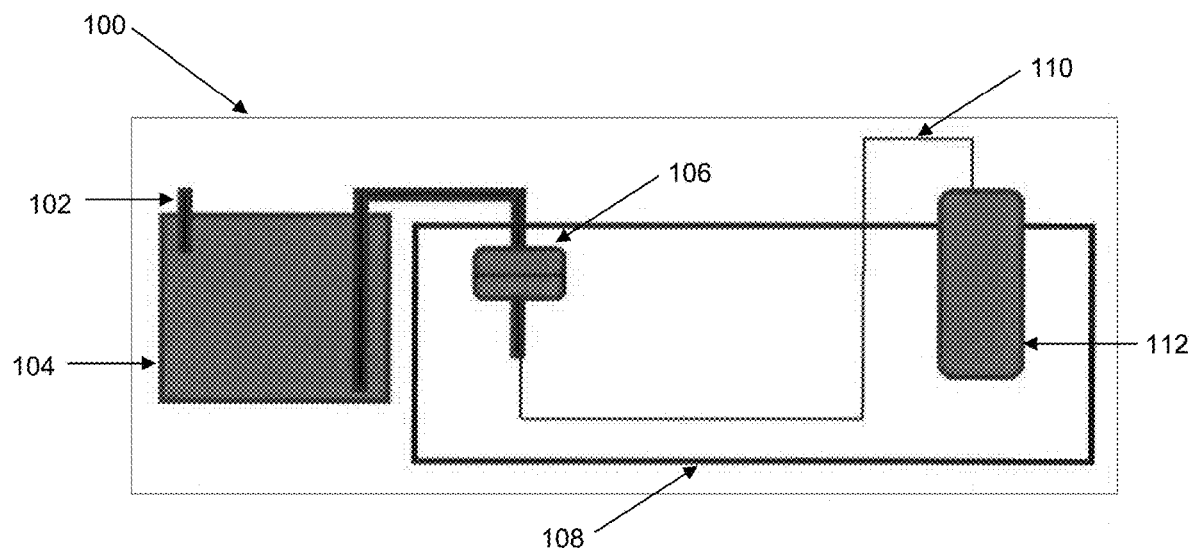
FIG. 1 is a schematic block diagram of a membrane extrusion setup 100 in an exemplary embodiment.

FIG. 1 is a schematic block diagram of a membrane extrusion setup 100 for preparing a dispersion of vesicles in an exemplary embodiment. The setup 100 comprises a gas inlet 102, which allows gas to be charged into a pressure vessel 104. The pressure vessel 104 is first loaded with a mixture of surfactant in water, which undergoes membrane extrusion via the action of gas charging through inlet 102 into pressure vessel 104 and forcing the mixture through filter holder 106 containing membranes of specific pore sizes (not shown). The outlet of filter holder 106 is connected with a Teflon tube 110, which leads to a collection flask 112 where the resulting filtrate is collected. The pressure vessel 104 is temperature controlled at 60-65° C. using heating tape (not shown). The filter holder 106 and collection flask 112 are temperature controlled using a water bath 108.

Figure 2A:
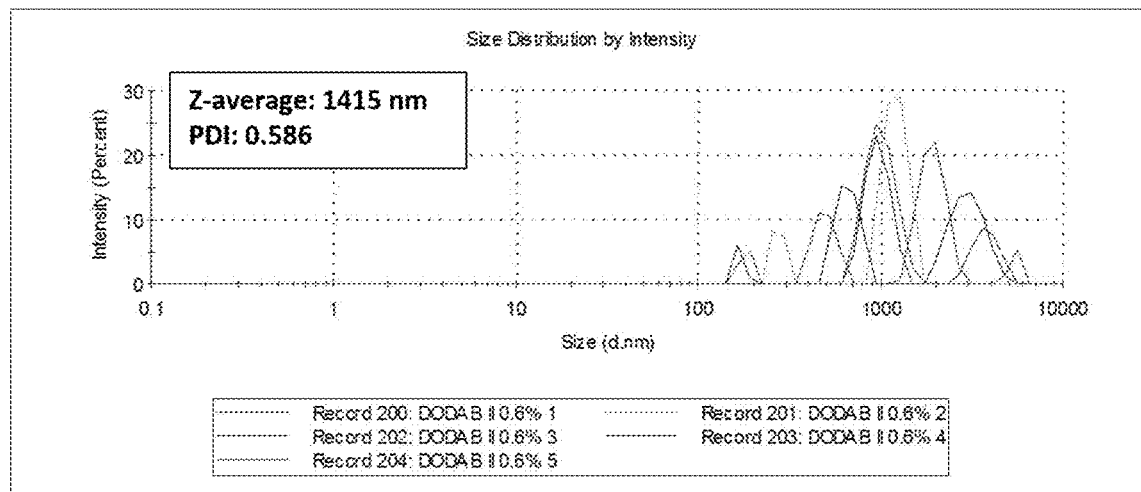
FIGS. 2A-2B are particle size distribution plots obtained from dynamic light scattering (DLS) measurements of a DODAB vesicle in accordance with various embodiments disclosed herein.
Figure 2B:
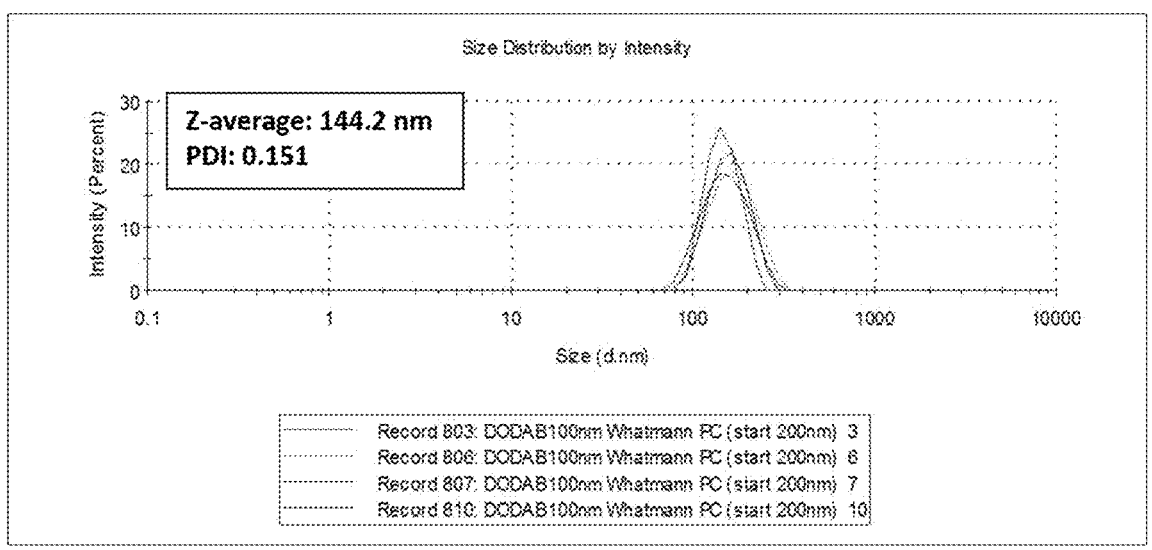

FIGS. 2A-2B are particle size distribution plots obtained from dynamic light scattering (DLS) measurements of a DODAB vesicle in accordance with various embodiments disclosed herein. FIG. 2A shows DLS measurements in a mixture of DODAB vesicle in water prior to membrane extrusion. FIG. 2B shows DLS measurements in a dispersion of DODAB vesicles after membrane extrusion using a polycarbonate membrane having a mean pore diameter of 400 nm. As shown, the particle size of a DODAB vesicle prior to membrane extrusion vary between 100 nm and 10,000 nm, with a z-average particle size of 1415 nm and a polydispersity index (PDI) of 0.586. After membrane extrusion, the average particle size of a DODAB vesicle is 144.2 nm.

Figure 3:
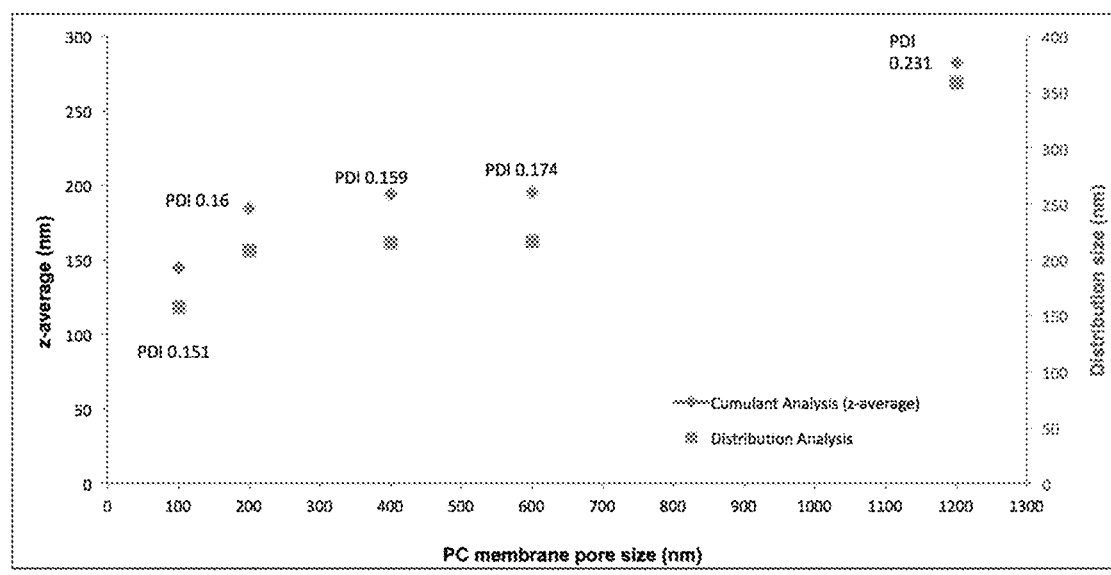
FIG. 3 is a graph showing variation in the z-average particle size of a DODAB vesicle obtained after different polycarbonate (PC) membrane pore sizes (100 nm, 200 nm, 400 nm, 600 nm and 1200 nm) are used in the membrane extrusion process in accordance with various embodiments disclosed herein.

FIG. 3 is a graph showing variation in the z-average particle size of a DODAB vesicle obtained after different polycarbonate (PC) membrane pore sizes (100 nm, 200 nm, 400 nm, 600 nm and 1200 nm) are used in the membrane extrusion process in accordance with various embodiments disclosed herein.

Figure 4A:
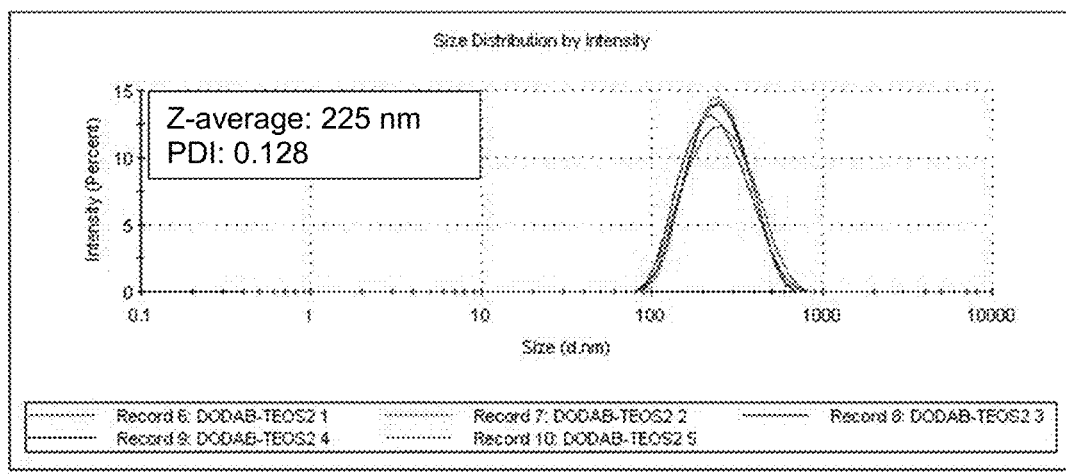
FIGS. 4A-4B are particle size distribution plots obtained from dynamic light scattering (DLS) measurements of silica nanocapsules in accordance with various embodiments disclosed herein.
Figure 4B:
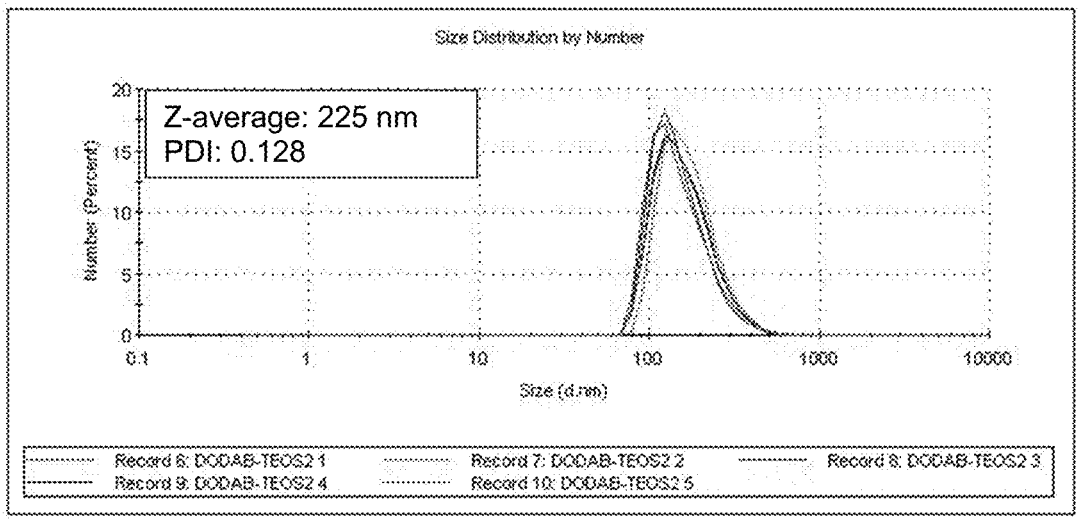

FIGS. 4A-4B are particle size distribution plots obtained from dynamic light scattering (DLS) measurements of silica nanocapsules in accordance with various embodiments disclosed herein. As shown, the particle size of the synthesized silica nanocapsules in accordance with various embodiments disclosed herein has a z-average particle size of 225 nm and a polydispersity index (PDI) of 0.128.

Figure 5:
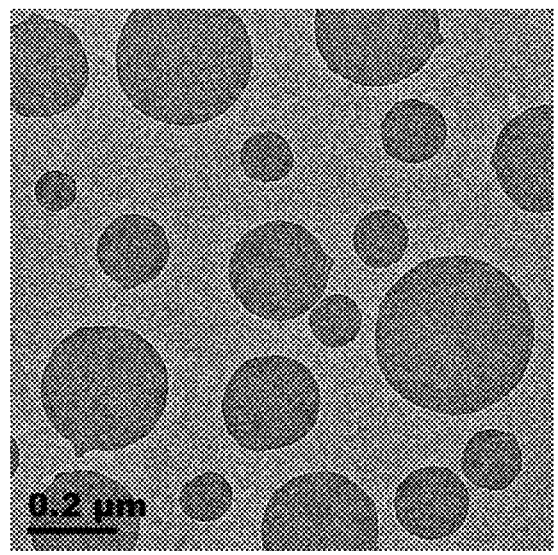

FIGS. 5, 6 and 7 are microscopic images of the synthesized silica nanocapsules in accordance with various embodiments disclosed herein.

FIG. 5 shows a conventional transmission electron microscopy (TEM) image of the hollow silica lens structure in solutions, with the scale bar representing 0.2 μm.

Figure 6A:
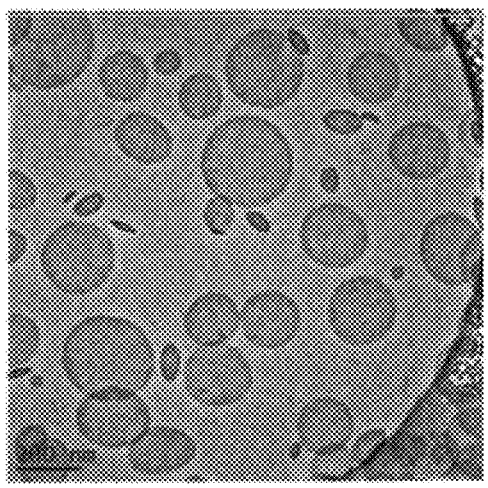
FIGS. 6A-6C show cryogenic transmission electron microscopy (cryo-TEM) images of the hollow silica lens structure in solutions in accordance with various embodiments disclosed herein.
Figure 6B:
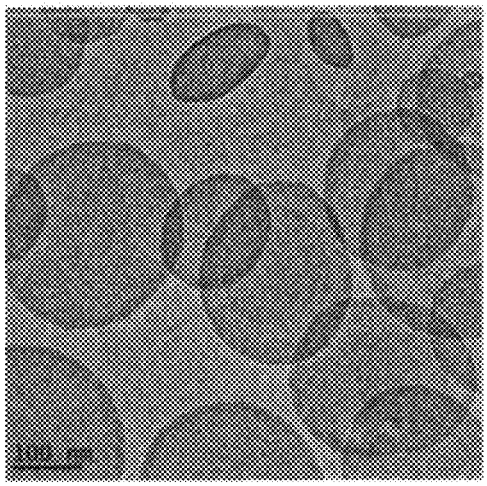
Figure 6C:
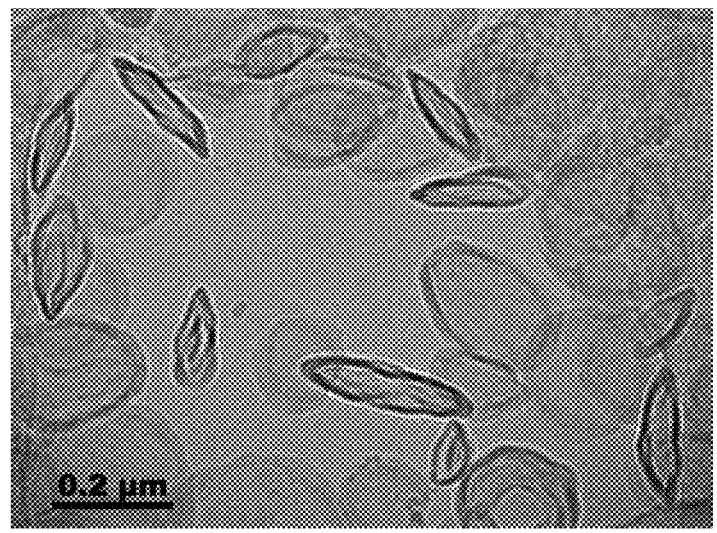

FIGS. 6A-6C show cryogenic transmission electron microscopy (cryo-TEM) images of the hollow silica lens structure in solutions. In FIG. 6A, the scale bar represents 200 nm. In FIG. 6B, the scale bar represents 100 nm. In FIG. 6C, the scale bar represents 0.2 μm. As shown, the hollow silica lens particles in solution appeared as spherical in shape.

Figure 7A:
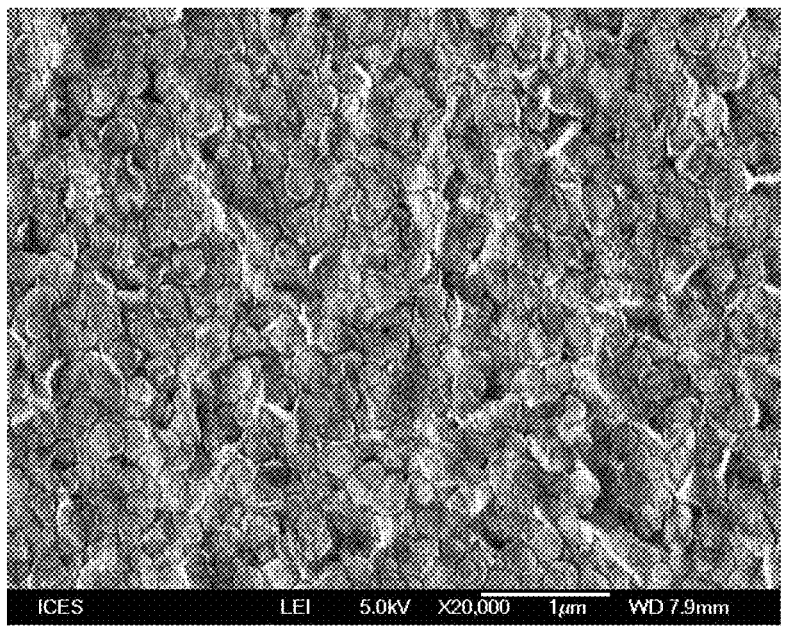
FIGS. 7A-7D show scanning electron microscopy (SEM) images of dried hollow silica lens structure in accordance with various embodiments disclosed herein.
Figure 7B:
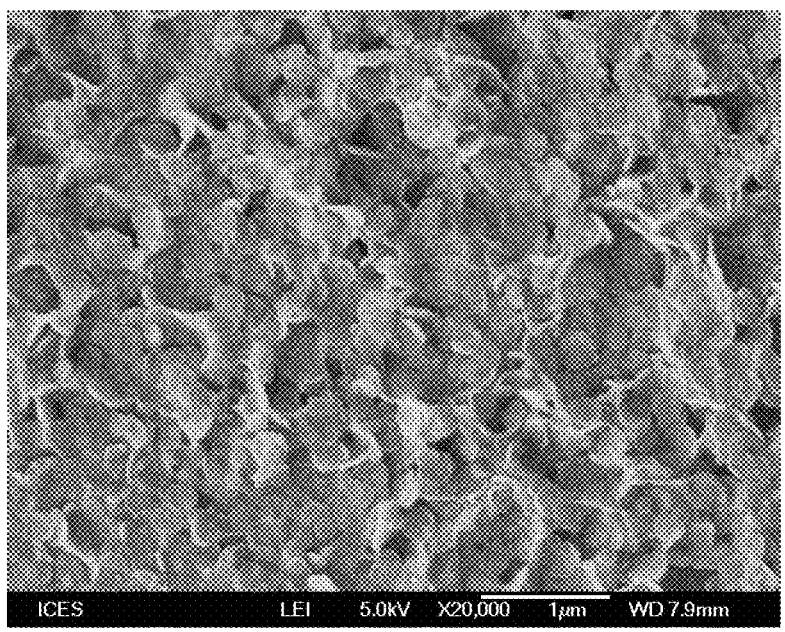
Figure 7C:
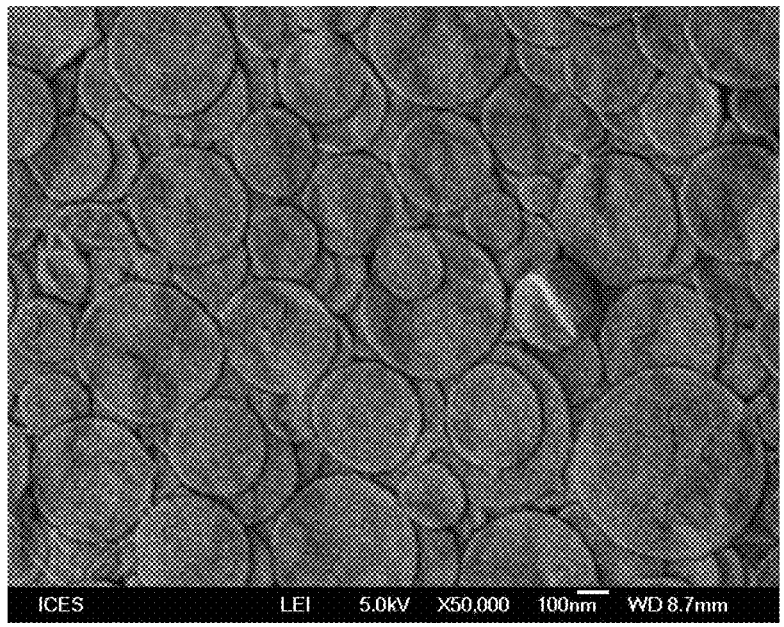
Figure 7D:
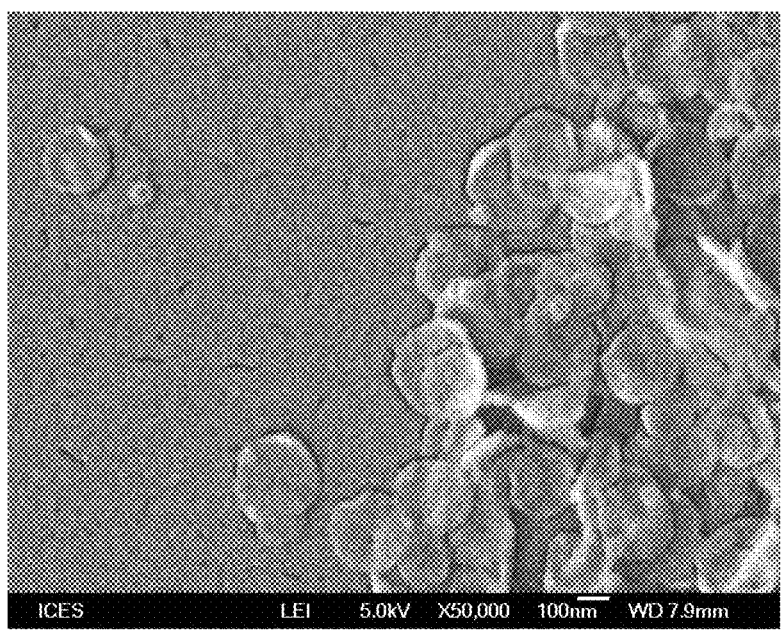

FIGS. 7A-7D show scanning electron microscopy (SEM) images of dried hollow silica lens structure. In FIG. 7A, the scale bar represents 1 μm. In FIG. 7B, the scale bar represents 1 μm. In FIG. 7C, the scale bar represents 100 nm. In FIG. 7D, the scale bar represents 100 nm. As shown, the dried hollow silica lens particles are lens-shaped.

Figure 8A:
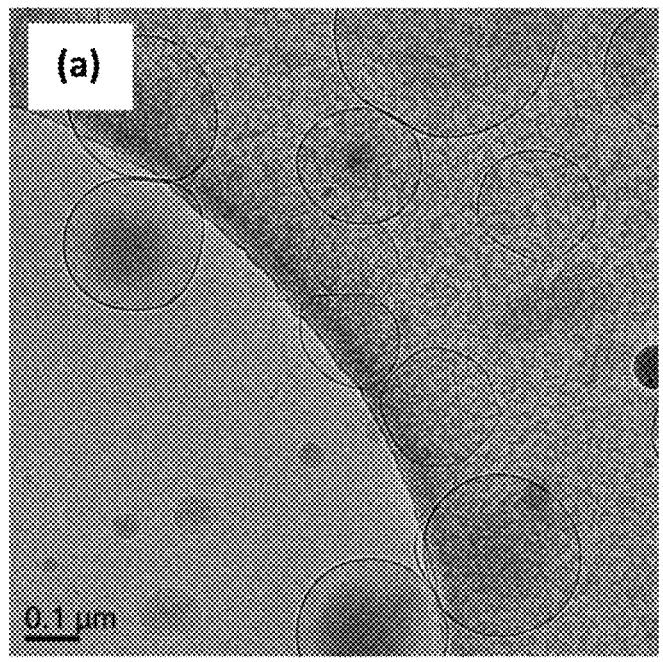
FIGS. 8A-8B show cryogenic transmission electron microscopy (cryo-TEM) images of DODAB vesicles in accordance with various embodiments disclosed herein.
Figure 8B:
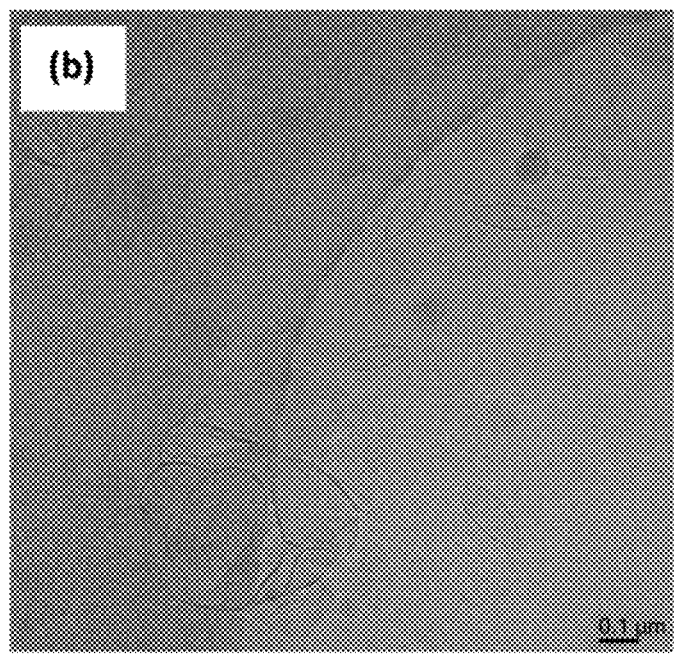

FIGS. 8A-8B show cryogenic transmission electron microscopy (cryo-TEM) images of DODAB vesicles in accordance with various embodiments disclosed herein. FIG. 8A shows a cryo-TEM image of DODAB vesicles before addition of ethanol, with the scale bar representing 0.1 μm. FIG. 8B shows a cryo-TEM image of DODAB vesicles after addition of ethanol, with the scale bar representing 0.1 μm. As shown, the DODAB vesicle is spherical in shape before addition of ethanol. After addition of ethanol, the DODAB vesicle becomes lens-shaped.

Figure 9:
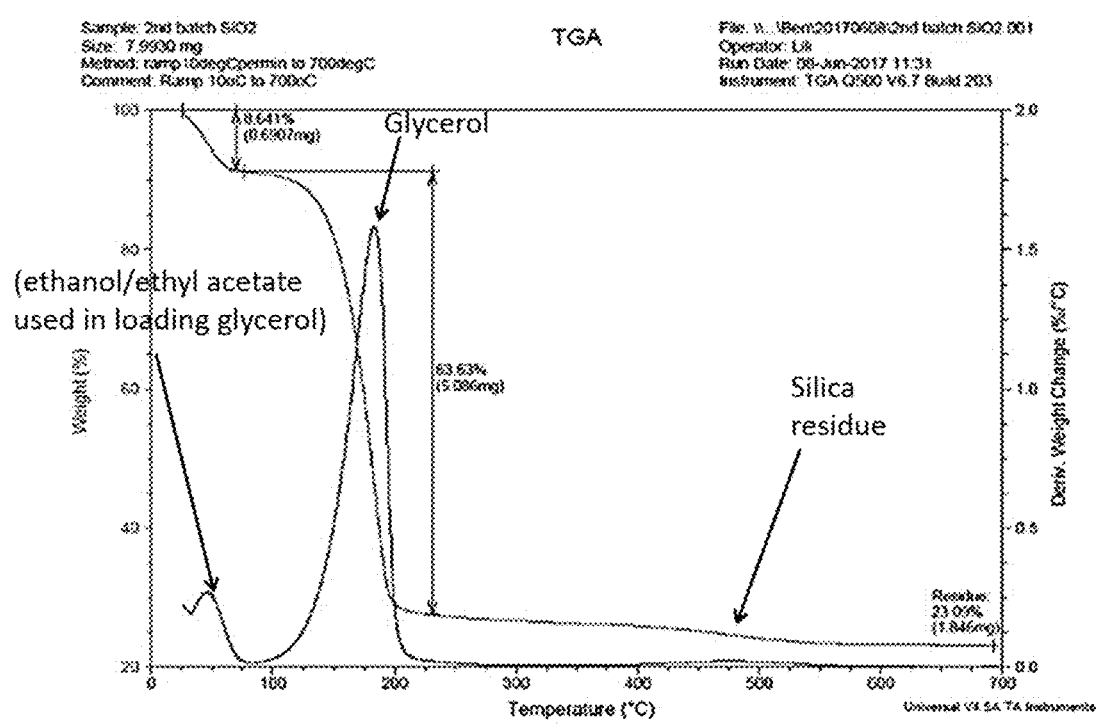
FIG. 9 is a graph showing the thermogravimetric profiles of glycerol loaded silica nanocapsules in accordance with various embodiments disclosed herein.

FIG. 9 is a graph showing the thermogravimetric profiles of glycerol loaded silica nanocapsules in accordance with various embodiments disclosed herein.

Figure 10A:
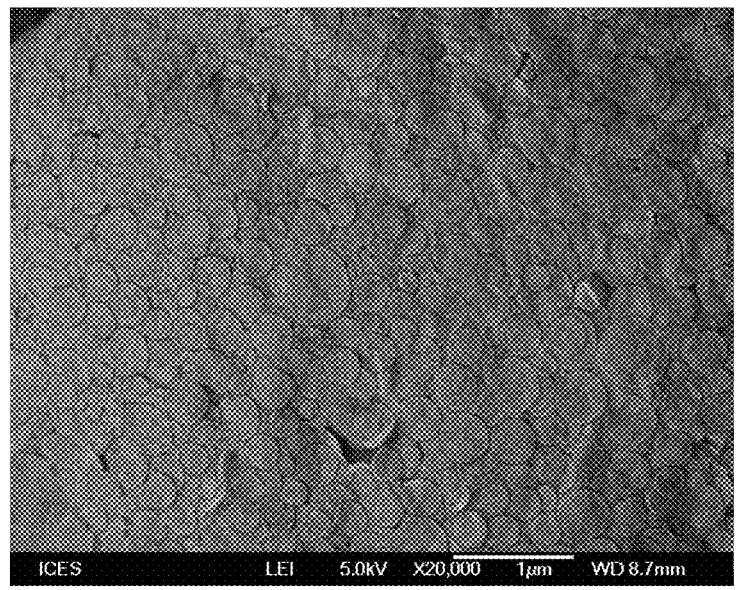
FIGS. 10-11 are microscopic images of synthesized silica nanocapsules (before and after glycerol loading) in accordance with various embodiments disclosed herein.
Figure 10B:
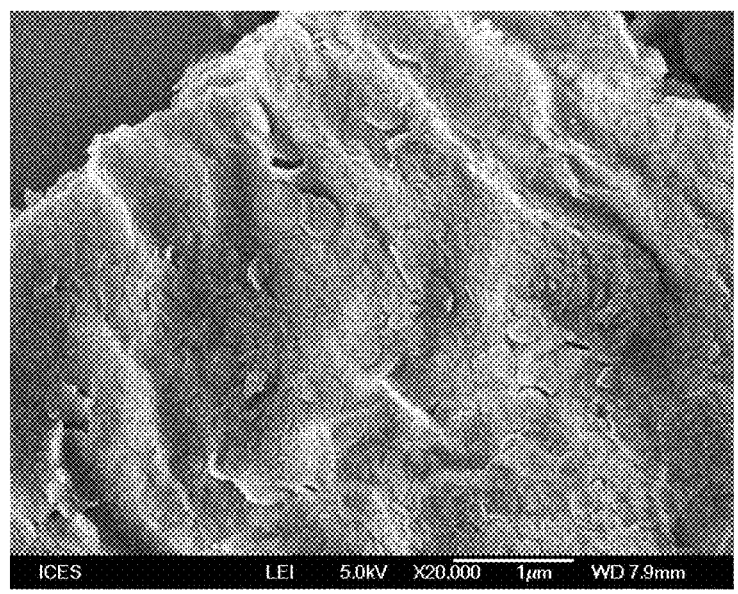
Figure 11A:
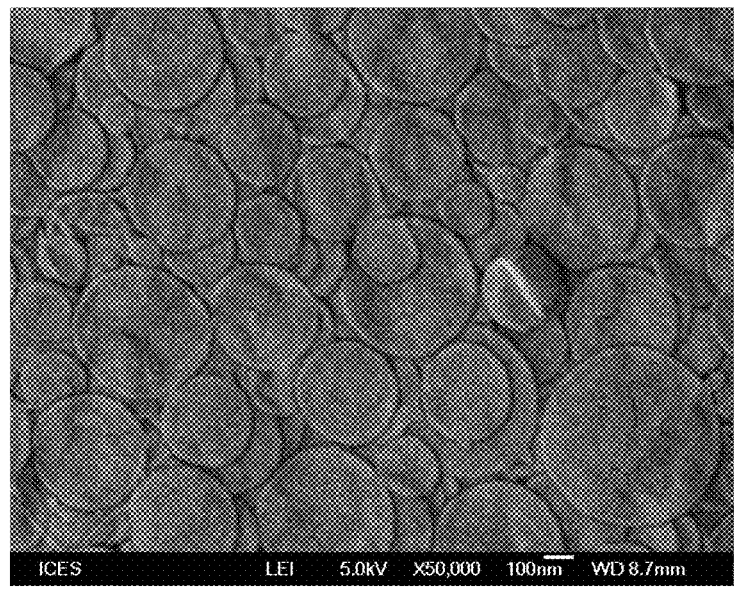
Figure 11B:
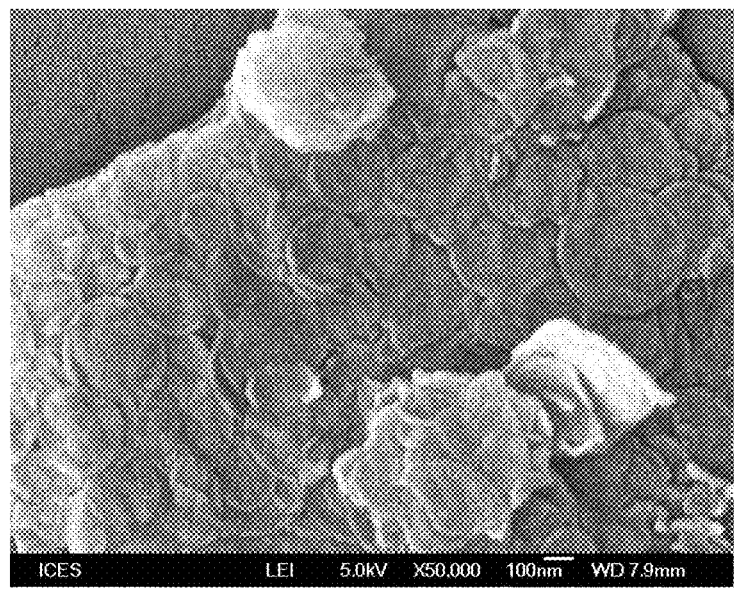

FIGS. 10-11 are microscopic images of synthesized silica nanocapsules (before and after glycerol loading) in accordance with various embodiments disclosed herein. FIGS. 10A and 11A show SEM images of silica nanocapsules prior to loading glycerol. FIGS. 10B and 11B show SEM images of glycerol loaded silica nanocapsules. As shown, there is no substantial change to the morphology of the silica nanocapsules after glycerol is loaded. The silica nanocapsules remained lens-shaped.

Figure 12:
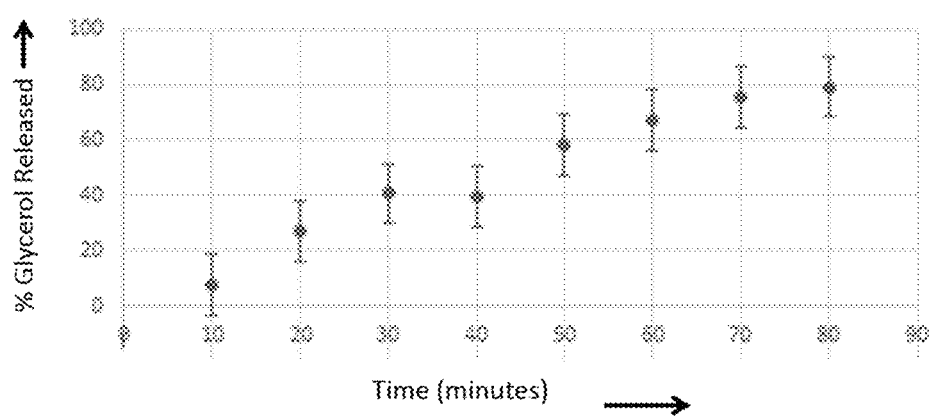
FIG. 12 is a graph showing the percentage release of glycerol over time from glycerol loaded silica nanocapsules in accordance with various embodiments disclosed herein.

FIG. 12 is a graph showing the percentage release of glycerol over time from glycerol loaded silica nanocapsules in accordance with various embodiments disclosed herein. As shown, encapsulated glycerol is released from the lens shaped particles approximately over a period of two hours.

Figure 13:
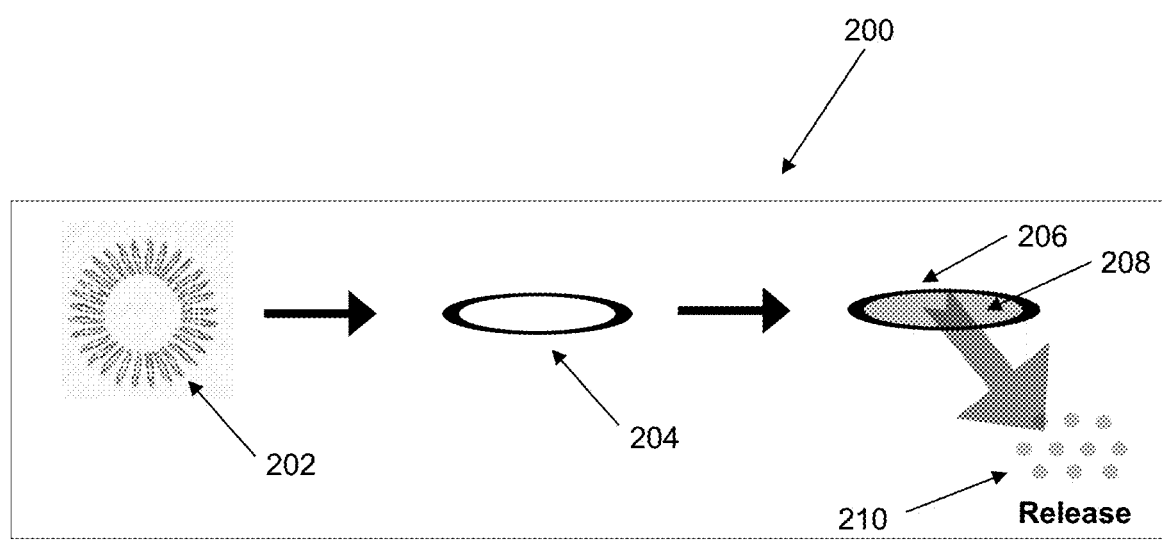
FIG. 13 shows a broad scheme 200 of synthesizing a silica nanocapsule from a vesicle in accordance with various embodiments disclosed herein.

FIG. 13 shows a broad scheme 200 of synthesizing silica nanocapsule 204 from a vesicle 202 in accordance with various embodiments disclosed herein. As shown in the figure, silica nanocapsule 204 having substantially lens-shaped morphology are obtained from using vesicle 202 as a template. The silica nanocapsule may be further loaded with one or more types of cargo, for example hydrophilic actives in its empty/hollow core 208 and subsequently act as a carrier for delivery and controlled release of the active molecules 210.

EXAMPLES

Example embodiments of the disclosure will be better understood and readily apparent to one of ordinary skill in the art from the following examples and if applicable, in conjunction with the figures.

The examples describe a method of preparing silica nanocapsules in a simple and direct process in accordance with various embodiments of the present disclosure. As will be shown in the following examples, embodiments of the presently disclosed method provide a cost-effective strategy to produce silica nanocapsules as elevated temperature and etching procedures were avoided and stable colloidal formulations (dispersion of vesicles) were formed in the absence of organic solvent. In summary, embodiments of the presently disclosed method require easy preparation and can be scaled up at ambient temperature without any specialized external energy inputs.

As will be shown in the following examples, embodiments of the presently disclosed method synthesize silica nanocapsules having substantially lens-shaped morphology with well controlled structure size and aspect ratio in the nanoscale. The particle size and shape can be carefully tuned to give a unique lens-shaped morphology with a pore size of as low as 190 nm. These len-shaped silica nanocapsules showed high reproducibility and stability in water as compared to spherical silica microcapsules. These len-shaped silica nanocapsules can be configured to allow loading of hydrophilic molecules in a high loading capacity (of at least about 50%), which are useful in a wide array of applications.

Example 1

Preparation of Vesicle Template

In this example, the preparation of vesicle template for the production of hollow silica nano lenses is demonstrated by using surfactant vesicle, for eg. dimethyldioctadecylammonium bromide (DODAB) or dioctadecyldimethyl-ammonium chloride (DODAC) as a soft template.

Firstly, large unilamellar vesicles (LUV) were prepared by a membrane extrusion method. As shown in FIG. 1, the membrane extrusion setup 100 contains a high pressure stainless steel (SS) pressure vessel 104, which is connected to a SS filter holder 106 containing three stacked Isopore 47 mm polycarbonate (PC) membranes (Merck Millipore, 47 mm). The outlet of the filter holder was connected with a Teflon tube 110, from which the filtrate was then collected into a flask 112. The whole setup was temperature controlled at 60-65° C. using a heating tape for the pressure vessel and a water bath 108 for the filter holder and collection flask.

Prior to extrusion, 0.631 wt % (10 mM) of DODAB or DODAC was prepared in aqueous solution and hydrated at 60° C., which is above the gel-to-liquid transition temperature (Tm) of DODAB or DODAC of 44° C., for 18 hrs under constant stirring speed of 300 rpm (using a 4-bladed stirrer at 45° C.). This was followed by loading into a pressure vessel 104 equipped with 7 bar argon.

Extrusion was started by charging the argon into the pressure vessel 104 which forced the liquid through 200-400 nm polycarbonate membranes. The filtrate was collected into a collection flask 112 and immediately charged back into the pressure vessel 104 for a second extrusion. After each extrusion, the size of the vesicles was determined by dynamic light scattering (DLS). A total of 8 cycles of extrusion was completed and the resulting vesicles dispersion appeared as a nice bluish dispersion, which was allowed to cool to room temperature naturally.

The following DLS size characterization results demonstrate the effectiveness of size control using the membrane extrusion method described herein. As will be shown in the following figures, the results indicated that a dispersion of DODAB vesicles having substantially uniform size is prepared successfully with membrane extrusion.

As shown in FIG. 2A, prior to membrane extrusion, a DODAB vesicle has a broad particle size distribution. The particle size vary over a wide range between 100 nm and 10,000 nm with a polydispersity index (PDI) of 0.586. After undergoing membrane extrusion with a membrane having a mean pore diameter of 400 nm, the average size measured for a DODAB vesicle is about 144 nm with a polydispersity index (PDI) of 0.151 as shown in FIG. 2B, which is indicative of a narrow size distribution and a successful control of the particle size with the use of membrane extrusion in obtaining substantially uniform vesicles.

The effect of varying the pore size of the membrane used during extrusion on the average particle size of the resulting DODAB vesicle obtained was also studied and the results are shown in FIG. 3. The results indicated that by specifically selecting a suitable membrane pore size during membrane extrusion, the size of the vesicles can be carefully controlled to give substantially uniform DODAB vesicles of the desired size.

Example 2

Synthesis of Hollow Silica Nano Lenses Via Vesicle Templatinq

In this example, a direct synthesis of hollow silica nano lenses is demonstrated via vesicle templating. The experiments are conducted at a laboratory scale but it would be understood that a further scale-up of the method may be carried out, for example by scaling to an industrial process.

In a typical experiment, the vesicle solution was used for hollow silica nano lenses synthesis without adjustment of pH. The reaction was started in a sequential step by adding silicon precursor, i.e. silicon alkoxide to the vesicle dispersion via a programmed syringe pump. The silicon alkoxide used can be tetraethyl orthosilicate (TEOS) or tetramethyl orthosilicate (TMOS). The concentration of silica precursor can be changed, for example, the silica precursor is added to the vesicle solution at a ratio of [DODAB]:[silica precursor] =1:10, 1:20 or 1:30. The reaction mixture was then vigorously stirred.

At the beginning of the reaction, an emulsion was present which disappeared as the reaction proceeded. Without being bound by theory, it is believed that the presence of the emulsion is due to the formation of oil droplets by the hydrophobic silica precursor. As the reaction proceeded, the oil phase disappeared as a result of hydrolysis of the hydrophobic silica precursor. At every desired instant, the pH can be adjusted by addition of ammonia to influence the sol-gel chemistry of the silica growth. All experiments were performed at room temperature.

The samples were aged for at least 1 day before transmission electron microscopy (TEM) and scanning electron microscopy (SEM) visualization studies, and freeze dried to get a dried powder.

Characterization Studies of Hollow Silica Nano Lens Particles

Characterization studies of embodiments of the hollow silica nano lens particles were performed with various methods including dynamic light scattering (DLS), transmission electron microscopy (TEM) and scanning electron microscopy (SEM).

The following characterization results indicated that silica nanocapsules having well-controlled structure size and aspect ratio in the nanoscale were successfully synthesized with the method disclosed herein. Electron microscope images also reveal that silica nanocapsules having a substantially lens-shaped morphology were synthesized.

The size of the hollow silica nano lens was determined by dynamic light scattering (DLS). As shown in FIGS. 4A-4B, the average size of the hollow silica nano lens prepared according to the method disclosed herein is about 190-250 nm (z average is 225 nm), with a polydispersity index (PDI) of 0.128.

Two different electron microscopy methods were used to visualize the hollow silica lens structure in solutions, namely conventional transmission electron microscopy (TEM) and cryo-transmission electron microscopy (Cryo-TEM), while scanning electron microscopy (SEM) was used for imaging the dried hollow silica nano lens particles.

FIG. 5 shows the normal TEM image of the hollow silica lens structure in solutions. FIGS. 6A-6C show the cryo-TEM images of the hollow silica lens structure in solutions. FIGS. 7A-7D show the SEM images of the dried hollow silica lens structure. From the morphology study, the Cryo-TEM imaging in FIGS. 6A-6C shows that the particles in solutions appeared as spherical in shape. The SEM images FIGS. 7A-7D show that the dried particles are lens-shaped. It should be appreciated that when viewed in certain different orientations, the silica lens structure may appear as shapes other than lens-shaped even though there is at least one orientation at which the structure would be viewed as lens-shaped. For example, when SEM is used, due to the need to dry the sample on the grid, in some instances the hollow silica lens observed may be flat on the surface so they appear as circles, e.g. pancakes or flattened spheres. In cryo-TEM, where the wet sample is frozen, the ability to capture the nanocapsules in various orientations may be enhanced and thus in some instances the lens-shaped structure may be more apparent.

Example 3

Shape Change in DODAB Vesicle from Spherical to Lens-Shaped

In this example, the morphology of the DODAB template is studied with Cryo-TEM imaging to primarily examine the formation of the unique silica lens shape from the spherical DODAB vesicle template.

Without being bound by theory, it is believed that the shape change of DODAB template from spherical to lens-shaped is due to the presence of the organic solvent "ethanol" in water. DODAB vesicle has a self-assembled bilayer structure and is a flexible and permeable template in water media. During hydrolysis and condensation reaction of TEOS to form $SiO_2$, ethanol is generated as a side product on the DODAB bilayer. It is therefore believed that the presence of organic solvent "ethanol" in water leads to the shape change of DODAB template from spherical to lens-shaped.

The effect of ethanol on the morphology of the DODAB vesicle is demonstrated in FIGS. 8A and 8B using cryo-TEM imaging. FIG. 8A shows that before addition of ethanol, a DODAB vesicle has a spherical shape. After addition of ethanol, FIG. 8B shows that the DODAB vesicle is lens-shaped. Therefore, in summary, without being bound by theory, it is believed that the lens-shaped morphology of the synthesized silica nanocapsules in accordance with various embodiments disclosed herein may be attributed to the lens-shaped morphology of DODAB vesicle template formed via generation of ethanol during hydrolysis and condensation reaction of TEOS.

Example 4

Loading Capacity Studies Using Glycerol

In this example, the synthesized silica nanocapsules in accordance with various embodiments disclosed herein is loaded with hydrophilic molecules, for example, glycerol and studied by using SEM imaging. The loading capacity of synthesized silica nanocapsules in accordance with various embodiments disclosed herein for glycerol is also examined.

The loading capacity of hollow silica nano lens for glycerol is determined by a post loading process using ethanol and ethyl acetate (EA). Dried hollow silica nano lens particles were mixed with glycerol and ethanol solution. Ethyl acetate (EA) was added into the silica-glycerol ethanol mixture where silica and glycerol were mixed well and stirred for 30 mins. Ethanol was dissolved in EA and EA-insoluble glycerol was forced to stay in the silica nano lens in the EA mixture. Hydrophilic active loaded silica nano lens particles were rinsed with EA 3 times and dried at room temperature. Hydrophilic active loaded silica nano lens particles were characterized by thermogravimetric analysis (TGA) to measure loading capacity. As shown in FIG. 9, TGA result of the glycerol loaded silica nano lens indicated that the loading capacity was 40%. The results also indicated that the glycerol loaded silica nano lens are thermodynamically stable at high temperatures e.g., 200° C.

The different loading trials are provided in a table below. The weight of the silica nano lens particles was measured before and after loading of glycerol and the percentage of glycerol loaded was calculated. It was observed that the synthesized silica nano lens particles can be loaded with more than 60% of glycerol.

TABLE 1

Maximum loading of glycerol attained in different batches of silica lens particles performed in various experiments.

| Sample | Sample Name | Weight of Silica (before loading) (g) | Weight of Glycerol (g) | Weight of Silica (after loading) (g) | Percentage of glycerol loaded (%) |
| --- | --- | --- | --- | --- | --- |
| 1 | Silica Lens | 0.2982 | 0.5908 | 0.3767 | 60.31 |
| 2 | Silica Lens | 0.3031 | 0.7018 | 0.3968 | 64.53 |
| 3 | Silica Lens | 0.2959 | 0.6045 | 0.3160 | 58.55 |
| 4 | Silica Lens | 0.2454 | 0.5002 | 0.2836 | 55.024 |

Characterization Studies of Glycerol Loaded Silica Nano Lens Powder

FIGS. 10A and 11A show the SEM images of silica lens particles before glycerol is loaded. FIGS. 10B and 11B show the SEM images of silica lens particles after loading glycerol. As shown, there is no substantial change to the lens-shaped morphology of the silica nanoparticles after loading glycerol, which is evident that the silica nanoparticles having substantially lens-shaped are chemically and physically stable (e.g. no breakage).

Although silica nano powder is not biocompatible by inhalation, it may be appreciated by a person skilled in the art that loading glycerol in silica nano lens imparts a higher density on the silica nano lens powder. Reference is made to the density of glycerol at 1.26 g/cm$^3$. As a result, the loaded silica nano lens powder would not easily escape and disperse in air. Moreover, the glycerol loaded silica lens powder may be formulated with needed additives (surfactant, dye, essential oil, etc.) for further consumer care applications, thereby eliminating any chances of inhalation into the human body.

Example 5

Timed Release Studies of Glycerol Loaded Silica Nanocapsules

In this example, timed release studies were conducted on the glycerol loaded silica nanocapsules in accordance with various embodiments disclosed herein. Firstly, the synthesized silica nano lens particles were loaded with glycerol. Then, they were suspended in aqueous media and compared with controls.

The percentage of glycerol released from the lens-shaped particles over a period of 80 minutes is estimated using standard enzymatic assay and the results are shown in FIG. 12. In water, unencapsulated glycerol instantly dissolves. On the other hand, encapsulated glycerol is released gradually from the lens-shaped particles over a period of approximately two hours. Advantageously, this result indicates that the encapsulation of glycerol in the lens-shaped particles displayed potential in achieving a sustained release profile of moisturizing hydrophilic actives for long periods of time.

Applications

Various embodiments of the present disclosure provide silica nanocapsules that are submicron in size, have a unique morphology that is substantially lens-shaped and have well controlled structure size and have an aspect ratio in the nanoscale. For example, it has been shown that the particle size and shape can be carefully tuned to give a unique lens-shaped morphology with a pore size of as low as 190 nm. Embodiments of the silica nanocapsules disclosed herein showed high reproducibility and stability in water as compared to spherical silica microcapsules.

In various embodiments, the silica nanocapsules disclosed herein can be scalable and are a new class of nanocarriers that can be used in a wide array of applications such as in therapy, diagnostics, pharmaceuticals, cosmetics, cosmeceuticals and nutraceuticals.

In various embodiments, the silica nanocapsules disclosed herein have an outer shell which encapsulates a substantially hollow interior configured to allow loading of many different types of molecules (such as different hydrophilic actives) in a high loading capacity (of at least about 50%). For example, the silica nanocapsules disclosed herein have a high flexibility in loading various types of hydrophilic actives such as moisturizers (glycerol), water soluble dye, water soluble vitamins such as vitamins B, B6, C, riboflavin, and hydrophilic natural product.

In various embodiments, the silica nanocapsules disclosed herein are biocompatible and biodegradable. In various embodiments, the silica nanocapsules disclosed herein have an enhanced sensory effect on the skin and provide a good desirable feel to the skin, thus making them attractive for use as skin brighteners, night creams, facial masks, anti-agers and moisturizers in cosmetic, skin care and personal care applications.

Various embodiments of the present disclosure provide a simple and direct synthesis of the silica nanocapsules disclosed herein. For example, the process involves easy preparation from a soft vesicle template in the absence of debris. Stable colloidal formulation (dispersion of vesicles) is formed in the absence of organic solvents and harsh tedious procedures such as high temperature calcination and/or etching are not required, thereby making the production process efficient and cost-effective on a large scale. The present disclosure has demonstrated the principles involved, and opens the way for further scale-up in many applications.

It will be appreciated by a person skilled in the art that other variations and/or modifications may be made to the embodiments disclosed herein without departing from the spirit or scope of the disclosure as broadly described. The present embodiments are, therefore, to be considered in all respects to be illustrative and not restrictive.

The invention claimed is:

1. A method of preparing substantially lens-shaped cargo-loaded silica nanocapsules, the method comprising:
    mixing a surfactant with water at a temperature that is above the gel-to-liquid transition temperature of the surfactant to form a mixture, the surfactant being selected from the group consisting of tetra alkyl ammonium halide; dimethyldioctadecylammonium bromide (DODAB);
    dimethyldioctadecylammonium chloride (DODAC); sulfate, phosphate or acetate salt of dimethyldioctadecylammonium (DODAX); dimethyldioctadecenylammonium bromide (DDAB); dimethyldioctadecenylammonium chloride (DDAC); sulfate, phosphate, acetate salt of dimethyldioctadecenylammonium (DDAX); bromide, chloride, sulfate, phosphate or acetate salt of 1,2-dioleoyl-3-trimethylammonium propane (DOTAP); bromide, chloride, sulfate, phosphate or acetate salt of 1,2-dioleoyl-3-dimethylammonium propane (DODAP); bromide, chloride, sulfate, phosphate or acetate salt of N-[1-(2,3-dioleyloxy)propyl]-N,N,N-trimethylammonium (DOTMA), and combinations thereof;
    passing the mixture one or more times through at least one pore to obtain a dispersion of vesicles;
    adding a silica precursor to the dispersion of vesicles to form substantially lens-shaped silica nanocapsules, the silicon precursor being selected from the group consisting of tetramethyl orthosilicate (TMOS), tetraethyl orthosilicate (TEOS), tetrapropyl orthosilicate (TPOS), tetrabutyl ortho silicate (TBOS) and combinations thereof; and
    mixing one or more types of hydrophilic cargo molecules with the substantially lens-shaped silica nanocapsules in the presence of a first organic solvent prior to adding a second organic solvent, to load the one or more types of hydrophilic cargo molecules into the substantially lens-shaped silica nanocapsules thereby obtaining substantially lens-shaped cargo-loaded silica nanocapsules,
    wherein the one or more types of hydrophilic cargo molecules is miscible with the first organic solvent,
    wherein the one or more types of hydrophilic cargo molecules is not miscible with the second organic solvent and
    wherein the first and second organic solvents are miscible with each other.

2. The method according to claim 1, wherein the step of adding a silica precursor to the dispersion of vesicles results in the silica precursor reacting with the vesicles to generate an organic solvent.

3. The method according to claim 2, wherein the organic solvent generated from the reaction between the silica precursor and the vesicles causes the shape of the vesicles to change from a substantially spherical shape to a substantially lens shape.

4. The method according to claim 1, wherein the at least one pore has a size of from 100 nm to 1300 nm.

5. The method according to claim 1, wherein the step of passing the mixture one or more times through at least one pore comprises passing the mixture at least four times through the at least one pore to reach a dispersion of vesicles having a bluish hue.

6. The method according to claim 1, wherein the step of adding a silica precursor to the dispersion of vesicles to form substantially lens-shaped silica nanocapsules is carried out under ambient conditions and/or wherein the silica precursor is added in an amount such that the surfactant to silica precursor ratio is from 1:5 to 1:40.

7. The method according to claim 1, further comprising non-thermally drying the substantially lens-shaped silica nanocapsules to obtain a powdered form of substantially lens-shaped silica nanocapsules.

8. The method according to claim 1, further comprising coagulating and/or filtrating the mixture/solution containing the one or more types of hydrophilic cargo molecules, the substantially lens-shaped silica nanocapsules, the first organic solvent and the second organic solvent to obtain the substantially lens-shaped cargo-loaded silica nanocapsules.

9. The method according to claim 1, wherein the method is substantially devoid of the addition of an organic solvent, the addition of a strong acid, the use of etching and the use of calcination, for the removal of a template used to form the substantially lens-shaped silica nanocapsules.

10. The method according to claim 1, wherein the first organic solvent comprises alcohol and the second organic solvent comprises ester.

\* \* \* \* \*